(12) United States Patent
Ostadrahimi et al.

(10) Patent No.: US 9,448,187 B2
(45) Date of Patent: Sep. 20, 2016

(54) IMAGING USING PROBES

(75) Inventors: Majid Ostadrahimi, Winnipeg (CA);
Joe Lovetri, Winnipeg (CA); Lotfollah Shafai, Winnipeg (CA)

(73) Assignee: University of Manitoba, Winnipeg (CA)

(*) Notice: Subject to any disclaimer, the term of this patent is extended or adjusted under 35 U.S.C. 154(b) by 443 days.

(21) Appl. No.: 14/127,288

(22) PCT Filed: Jun. 26, 2012

(86) PCT No.: PCT/IB2012/053228
§ 371 (c)(1),
(2), (4) Date: Apr. 8, 2014

(87) PCT Pub. No.: WO2013/005134
PCT Pub. Date: Jan. 10, 2013

(65) Prior Publication Data
US 2014/0218230 A1    Aug. 7, 2014

Related U.S. Application Data

(60) Provisional application No. 61/503,783, filed on Jul. 1, 2011.

(51) Int. Cl.
*A61B 5/05* (2006.01)
*G01S 13/89* (2006.01)
*G01N 22/00* (2006.01)
(Continued)

(52) U.S. Cl.
CPC ............ *G01N 22/00* (2013.01); *A61B 5/0507* (2013.01); *G01S 13/89* (2013.01)

(58) Field of Classification Search
CPC ...... G01N 22/00; A61B 5/05; A61B 5/0507; H01Q 1/36; H01Q 1/38; H01Q 15/02; H01Q 15/04; G01R 29/08; G01R 29/10; G01S 13/88; G01S 13/89
See application file for complete search history.

(56) References Cited

U.S. PATENT DOCUMENTS

| | | | |
|---|---|---|---|
| 5,051,748 A | 9/1991 | Pichot et al. | |
| 5,430,369 A | 7/1995 | Bolomey et al. | |
| 5,627,553 A * | 5/1997 | Poulton | H01Q 15/04 333/21 A |

(Continued)

FOREIGN PATENT DOCUMENTS

| | | |
|---|---|---|
| WO | WO 2009/066186 A2 | 5/2009 |
| WO | WO 2009/066186 A3 | 7/2009 |

(Continued)

OTHER PUBLICATIONS

Abubakar et al. "Non-linear three-dimensional inversion of cross-well electrical measurements". 2000. *Geophysical Prospecting.* 48(1):109-134.

(Continued)

*Primary Examiner* — Bernarr Gregory
(74) *Attorney, Agent, or Firm* — Mueting, Raasch & Gebhardt, P.A.

(57) ABSTRACT

Methods and systems may image an object of interest using one or more probes. More specifically, such exemplary methods and systems may deliver electromagnetic energy (e.g., microwave energy) using a transmitting antenna to the object while activating a probe to interact with the scattered field and sampling the resulting scattered field using one or more receiving antennas. The sampled electromagnetic energy may then be used to reconstruct an image of the object.

34 Claims, 20 Drawing Sheets

(51) Int. Cl.
A61B 5/00 (2006.01)
G01S 13/00 (2006.01)

(56) References Cited

U.S. PATENT DOCUMENTS

| | | | |
|---|---|---|---|
| 5,715,819 A | 2/1998 | Svenson et al. | |
| 6,448,788 B1* | 9/2002 | Meaney | A61B 5/0507 324/637 |
| 6,490,471 B2 | 12/2002 | Svenson et al. | |
| 6,777,684 B1 | 8/2004 | Volkov et al. | |
| 6,885,191 B1* | 4/2005 | Gleman | A61B 5/05 324/300 |
| 6,965,340 B1 | 11/2005 | Baharav et al. | |
| 7,167,133 B2* | 1/2007 | Nagashima | G01R 29/10 324/637 |
| 7,439,736 B2* | 10/2008 | Meaney | A61B 5/05 324/307 |
| 7,746,266 B2 | 6/2010 | Zoughi et al. | |
| 7,825,667 B2* | 11/2010 | Fang | A61B 5/05 324/637 |
| 7,843,347 B2* | 11/2010 | Nikitin | H01Q 1/38 340/10.1 |
| 8,724,864 B2* | 5/2014 | Persson | 382/128 |
| 2004/0077943 A1* | 4/2004 | Meaney | A61B 5/05 600/430 |
| 2006/0239404 A1 | 10/2006 | Udpa et al. | |
| 2006/0293597 A1 | 12/2006 | Johnson et al. | |
| 2007/0015993 A1 | 1/2007 | Ciocan et al. | |
| 2011/0040176 A1* | 2/2011 | Razansky | A61B 5/05 600/425 |
| 2011/0137381 A1 | 6/2011 | Lee et al. | |
| 2011/0227586 A1 | 9/2011 | Lovetri | |
| 2012/0191148 A1 | 7/2012 | McKenna et al. | |

FOREIGN PATENT DOCUMENTS

| | | |
|---|---|---|
| WO | WO 2010/049523 A1 | 5/2010 |
| WO | WO 2013/005134 | 1/2013 |

OTHER PUBLICATIONS

Abubakar et al. "Imaging of biomedical data using a multiplicative regularized contrast source inversion method". 2002. *IEEE Trans. Microw. Theory Tech.* 50(7):1761-1771.
Abubakar et al. "The contrast source inversion method for location and shape reconstructions". 2002. *Inverse Problems.* 18-495:510.
Abubakar et al. "A robust iterative method for Born inversion". 2004. IEEE Trans. Geosci. Remote Sensing. 42(2):342-354.
Abubakar et al. "2.5d forward and inverse modeling for interpreting low frequency electromagnetic measurements". 2008. *Geophysics.* 73(4):F165-177.
Abubakar et al. "Iterative forward and inverse algorithms based on domain integral equations for three-dimensional electric and magnetic objects" 2004. *J. Comput. Phys.* 195(1):236-262.
Abubakar et al. "A multiplicative regularization approach for deblurring problems". 2004. IEEE Trans. Image. Process. 13(11):1524-1532.
Bolomey et al. Engineering applications of the modulated scatterer technique. Artech House Publishers. 2001.Title Page, Copyright Page, Table of Contents.
Bolomey et al. "On the possible use of microwave-active imaging for remote thermal sensing". 1983. *IEEE Trans. Microw. Theory Tech.*, 31(9):777-781.
Broquetas et al., "Cylindrical geometry: a further step in active microwave tomography". 1991. IEEE Trans. Microwave Theory Tech. 39(5):836-844.
Bulyshev et al., "Three dimensional microwave tomography. Theory and computer experiments in scalar approximation," *Inverse Problems*, Jun. 2000; 16(3): 863-875.
Charbonnier et al., "Deterministic Edge-Preserving Regularization in Computed Imaging," *IEEE Trans. on Image Processing*, Feb. 1997; 6(2): 298-311.

Caorsi et al. "A passive antenna system for data acquisition in scattering applications". 2002. *Antennas and Wireless Propagation Letters, IEEE.* 1:203-206.
Chew et al. "Reconstruction of two-dimensional permittivity distribution using the distorted born iterative method" 1990. *IEEE Transactions* on. 9(2):218-225.
Crocco et al., "On embedded microwave imaging systems: retrievable information and design guidelines," *Inverse Problems*, Mar. 27, 2009; 25(6): 065001 (17 pgs).
Cullen et al. "A new perturbation method for measuring microwave fields in free space". 1955. *Proceedings of the IEE-Part B: Radio and Electronic Engineering.* 102(6):836-844.
De Zaeytijd et al. "Full-wave three-dimensional microwave imaging with a regularized Gauss-Newton method theory and experiment". 2007. Antennas and Propagation, IEEE Transactions on 55(11):3279-3292.
Fang et al. "Viable three-dimensional medical microwave tomography: theory and numerical experiments" 2010. Antennas and Propagation, IEEE Transactions on 58(2):449-458.
Fear et al. "Microwave Detection of Breast Cancer". 2000. Microwave Theory and Techniques, IEEE Transactions. 48:1854-1863.
Fhager et al., "Reconstruction quality and spectral content of an electromagnetic time-domain inversion algorithm," *IEEE Trans. Biomed. Eng.*, Aug. 2006; 53(8): 1594-1604.
Franchois et al., "Quantitative microwave imaging with a 2.45-GHz planar microwave camera," *IEEE Trans. Med. Imaging*, Aug. 1998; 17(4): 550-561.
Franchois et al., "A quasi-Newton reconstruction algorithm for a complex microwave imaging scanner environment," *Radio Sci.*, Jan. 10, 2003; 38(2): 8011-8023.
Franza et al., "SICS: A sensor interaction compensation scheme for microwave imaging," *IEEE Trans. Antennas Propag.*, Feb. 2002; 50(2): 211-216.
Geffrin et al. "Continuing with the Fresnel database: experimental setup and improvements in 3D scattering measurements". 2009. Inverse Problems. 25:024001.
Ghasr et al. "Portable real-time microwave camera at 24 GHz". 2012. Antennas and Propagation, IEEE Transactions on 60(2):1114-1125.
Ghasr et al. "A novel 24 ghz one-shot, rapid and portable microwave imaging systems" 2008. *IEEE Instrum. Meas. Tech. Conf. Proceedings. IEEE.* pp. 1798-1802.
Gilmore et al., "Enhancement of microwave tomography through the use of electrically conducting enclosures," *Inverse Problems*, Apr. 8, 2008; 24(3): 035008 (21 pgs).
Gilmore et al., "Microwave Biomedical Data Inversion Using the Finite-Difference Contrast Source Inversion Method," *IEEE Trans. Antennas Propag.*, May 2009; 57(5): 1528-1538.
Gilmore et al. "A wideband microwave tomography system with a novel frequency selection procedure". 2010 *IEEE Trans. Biomed. Eng.* 57(4):894-904.
Gilmore et al. "On super-resolution with an experimental microwave tomography system". 2010. *IEEE Antennas Wireless Propag. Lett.* 9:393-396.
Gilmore et al., "Corrections to the 'Enhancement of microwave tomography through the use of electrically conducting enclosures,'" *Inverse Problems*, Jan. 2010; 26(1): 019801 (7 pgs.).
Gilmore et al. "The University of Manitoba microwave imaging repository: a two-dimensional microwave scattering database for testing inversion and calibration algorithms" 2011. Antennas and Propagation Magazine, IEEE. 53(5):126-133.
Gilmore et al. "A study of matching fluid loss in a biomedical microwave tomography system". 2013. *Medical Physics.* 40:023101.
Habashy et al., "A general framework for constraint minimization for the inversion of electromagnetic measurements," *Progress in Electromagnetics Research*, 2004; 46: 265-312.
Halter et al. "The correlation of in vivo and ex vivo tissue dielectric properties to validate electromagnetic breast imaging: initial clinical experience". 2009. *Physiological Measurement.* 30:S121.
Harrington. "Small resonant scatterers and their use for field measurements". 1962. *Microwave Theory and Techniques. IRE Transactions* on, 10(3):165-174.

(56) References Cited

OTHER PUBLICATIONS

Harrington. Time-harmonic electromagnetic fields. New York: IEEE Press: Wiley-Interscience. 2001. Title Page, Copyright Page, Table of Contents.
Henriksson et al. "Quantitative microwave imaging for breast cancer detection using a planar 2.45 GHz system". 2010. *IEEE Trans. Instrum. Meas.* 59(10):2691-2699.
Joachimowicz et al. "Inverse scattering: An Iterative numerical method for electromagnetic imaging". 1991. *IEEE Trans. Antennas Propag.* 39(12):1742-1753.
Kleinman et al. "A Modified gradient method for two-dimensional problems in tomography".1992. *Journ. of Computational and Applied Mathematics.* 42(1):17-35.
Klemm et al. "Radar-Based Breast Cancer Detection Using a Hemispherical Antenna Array—Experimental Results". 2009. Antennas and Propagation, IEEE Transactions. 57(6):1692-1704.
Lazebnik et al., "Highly Accurate Debye Models for Normal and Malignant Breast Tissue Dielectric Properties at Microwave Frequencies," *IEEE Microwave and Wireless Components Letters*, Dec. 2007; 17(12): 822-824.
Lencrerot et al., "Imposing Zernike representation for imaging two-dimensional targets," *Inverse Problems in Science and Engineering*, Feb. 3, 2009; 25(3): 035012 (21 pgs).
Lencrerot et al., "Measurement strategies for a confined microwave circular scanner," *Inverse Problems in Science and Engineering*, Sep. 2009; 17(6): 787-802. Available online Aug. 6, 2009.
LoVetri, "Computational electromagnetics and electromagnetic inverse imaging," Grant Abstract [online]. Natural Sciences and Engineering Research Council of Canada, project dates: fiscal year 2010-2011 [retrieved on Aug. 9, 2011]. Retrieved from the Internet: <URL: http://www.outil.ost.uqam.ca/CRSNG/Detail.aspx?Cle=451511&Langue=2>, 2 pgs.
Meaney et al., "Microwave imaging for tissue assessment: initial evaluation in multitarget tissue-equivalent phantoms," *IEEE Trans. Biomed. Eng.*, Sep. 1996; 43(9): 878-890.
Meaney et al., "Nonactive antenna compensation for fixed-array microwave imaging:Part II—Imaging results," *IEEE Trans. Med. Imaging*, Jun. 1999; 18(6): 508-518.
Meaney et al., "A clinical prototype for active microwave imaging of the breast," *IEEE Trans. Microwave Theory Tech.*, Nov. 2000; 48(11): 1841-1853.
Meaney et al., "Pre-scaled two-parameter Gauss-Newton image reconstruction to reduce property recovery imbalance," *Phys. Med. Biol.*, Apr. 7, 2002; 47(7): 1101-1119.
Meaney et al., "Initial clinical experience with microwave breast imaging in women with normal mammography," *Acad. Radiol.*, Feb. 2007; 14(2): 207-218.
Memarzadeh-Tehran et al. "Optically modulated probe for precision near-field measurements". 2010. *IEEE Trans. Instrum. Meas.* 59(10):2755-2762.
Mohassel. "Meander antennas". Ph.D. dissertation. The University of Michigan. 1982.
Mojabi et al. "Microwave biomedical imaging using the multiplicative regularized gauss-newton inversion". 2009. *IEEE Antennas Wireless Propag. Lett.*, 8:645-648.
Mojabi et al. "Overview and classification of some regularization techniques for the gauss-newton inversion method applied to inverse scattering problems". 2009. *IEEE Trans. Antennas Propag.* 57(9):2658-2665.
Mojabi et al., "Adapting the Normalized Cumulative Periodogram Parameter-Choice Method to the Tikhonov Regularization of 2-D/TM Electromagnetic Inverse Scattering Using Born Iterative Method," *Progress in Electromagnetics Research M*, 2008; 1: 111-138.
Mojabi et al., "Biomedical microwave inversion in conducting cylinders of arbitrary shapes," 13th *International Symposium on Antenna Technology and Applied Electromagnetics and the Canadian Radio Science Meeting (ANTEM/URSI)*, Toronto, Ontario, Feb. 15-18, 2009: 1-4.
Mojabi et al., "Enhancement of the Krylov subspace regularization for microwave biomedical imaging," *IEEE Trans. Med. Imaging*, Dec. 2009; 28(12): 2015-2019. Available online Jul. 24, 2009.
Mojabi et al., "Eigen function contrast source inversion for circular metallic enclosures," *Inverse Problems*, Feb. 2010; 26(2): 025010 (23 pgs.).
Mojabi et al., "Comparison of TE and TM Inversions in the Framework of the Gauss-Newton Method," *IEEE Trans. Antennas Propag.*, Apr. 2010; 58(4): 1336-1348.
Mojabi et al., "A Novel Microwave Tomography System Using a Rotatable Conductive Enclosure," *IEEE Transactions on Antennas and Propagation*, May 2, 2011; 59(5): 1597-1605. Available online Mar. 7, 2011.
Mojabi et al. "A multiplicative regularized gauss-newton inversion for shape and location reconstruction". 2011. Antennas and Propagation, IEEE Transactions. 59(12):4790-4802.
Nikolova. "Microwave imaging for breast cancer". 2011. *Microwave Magazine*, IEEE. 12(7):78-94.
O'Halloran et al., "Rotating Antenna Microwave Imaging System for Breast Cancer Detection," *Progress in Electromagnetics Research*, 2010; 107: 203-217.
Ostadrahimi et al. "A modified double layer tapered slot antenna with improved cross polarization" 2009. Antenna Tech. and App. Electromagn. NTEM/URSI. 13th Int. Symp. IEEE.
Ostadrahimi et al. "Investigating a double layer Vivaldi antenna design for fixed array field measurement". 2010. *Intl. Journ. of Ultra Wideband Communications and Systems.* 1(4):282-290.
Ostadrahimi et al. "Analysis of incident field modeling and incident/scattered field calibration techniques in microwave tomography". 2011. Antennas and Wireless Propagation Letters, IEEE. 10:900-903.
Ostadrahimi et al. "A multiprobe-per-collector modulated scatterer technique for microwave tomography". 2011. Antennas and Wireless Propagation Letters. IEEE. 10:1445-1448.
Ostadrahimi et al. "A novel microwave tomography system based on the scattering probe technique". 2012. Instrumentation and Measurement. IEEE Transactions. 61(2):379-390.
Ostadrahimi et al. "A near-field dual polarized TE-TM microwave imaging system". 2013. Microwave Theory and Techniques, IEEE Transactions. 61(3):1376-1384.
Ostadrahimi et al. "Enhancement of Gauss-Newton inversion method for biological tissue imaging". 2013. Microwave Theory and Techniques, IEEE Transactions on, 61(9):3424-3434.
Ostadrahimi et al. "An mst-based microwave tomography system using homodyne receiver". 2013. IEEE Intl. Symp. on Antennas and Propagation and USNC/URSI National Radio Science Meeting. IEEE. pp. 1-4.
Pastorino, "Stochastic Optimization Methods Applied to Microwave Imaging: A Review," *IEEE Trans. Antennas Propag.*, Mar. 2007; 55(3): 538-548.
Pastorino. Microwave Imaging. John Wiley & Sons. 2010. Title Page, Copyright Page, Table of Contents.
Paulsen et al., "Nonactive antenna compensation for fixed-array microwave imaging—Part I: Model development," *IEEE Trans. Med. Imag.*, Jun. 1999; 18(6): 496-507.
Rubaek et al., "Nonlinear Microwave Imaging for Breast-Cancer Screening Using Gauss-Newton's Method and the CGLS Inversion Algorithm," *IEEE Trans. Antennas Propag.*, Aug. 2007; 55(8): 2320-2331.
Rubaek et al., "Computational Validation of a 3-D Microwave Imaging System for Breast-Cancer Screening," *IEEE Transactions Antennas and Propag.*, Jul. 2009; 57(7): 2105-2115.
Semenov et al. "Spatial resolution of microwave tomography for detection of myocardial ischemia and infarction-experimental study on two-dimensional models". 2000. *IEEE Trans. Microw. Theory Tech.* 48(4):538-544.
Semenov et al., "Three-dimensional microwave tomography: initial experimental imaging of animals," *IEEE Trans. Biomed. Eng.*, Jan. 2002; 49(1): 55-63.
Semenov et al. "Microwave-tomographic imaging of the high dielectric-contrast objects using different image-reconstruction approaches". 2005. *IEEE Trans. Microw. Theory Tech.* 53(7):2284-2294.

(56) References Cited

OTHER PUBLICATIONS

Semenov et al. "Microwave tomography of extremities: 1. Dedicated 2D system and physiological signatures". 2011. Physics in Medicine and Biology. 56(7):2005-2017.

Semenov et al. "Microwave tomography: review of the progress towards clinical applications". 2009. *Philos Transact a Math Phys Eng Sci.* 367(12900):3021.

Stang et al. "A preclinical system prototype for focused microwave thermal therapy of the breast". 2012. Biomedical engineering, IEEE Transactions.

Tijhuis et al., "Theoretical and Computational Aspects of 2-D Inverse Profiling," *IEEE Trans. Geosci. Remote Sensing*, Jun. 2001; 39(6): 1316-1330.

van den Berg et al. "A contrast source inversion method", 1997. *Inverse Problems.* 13:1607-1620.

Vardalahos. "Investigation of loaded monopole antenna". Ph.D. dissertation. Msc. Thesis. University of Leeds. 2000.

Wadbro et al., "Microwave Tomography Using Topology Optimization Techniques," *SIAM J. Sci. Comput.*, Mar. 2008; 30(3): 1613-1633.

Wang et al., "An iterative solution of the two-dimensional electromagnetic inverse scattering problem," *Int. J. Imag. Syst. Technol.*, Sum. 1989; 1(1): 100-108. Available online Oct. 20, 2005.

Yu et al., "Active Microwave Imaging II: 3-D System Prototype and Image Reconstruction From Experimental Data," *IEEE Trans. Microwave Theory Tech.*, Apr. 2008; 56(4): 991-1000.

Zaeytijd et al., "Full-Wave Three-Dimensional Microwave Imaging With a Regularized Gauss-Newton Method-Theory and Experiment," *IEEE Trans. Antennas Propag.*, Nov. 2007; 55(11): 3279-3292.

Zakaria et al. "Finite-element contrast source inversion method for microwave imaging". 2010. Inverse Problems. 26:115010. 21 pages.

Zakaria et al. "The finite-element method contrast source inversion algorithm for 2d transverse electrical vectorial problems". 2012. Antennas and Propagation, IEEE Transactions. 60(10):4757-4765.

Zakaria et al. "Application of multiplicative regularization to the finite-element contrast source inversion method". 2011. IEEE Tran. on Antenn. and Propag. 59:3495-3498.

Zakaria et al. "Full-vectorial parallel finite-element contrast source inversion method". 2013. Progress in Electromagnetics Research. 142:463-483.

International Preliminary Report on Patentability, issued by the European Patent Office on Jan. 16, 2014 in related Application No. PCT/IB2012/053228.

Written Opinion, issued by the European Patent Office on Jan. 16, 2014, in related Application No. PCT/IB2012/053228.

International Search Report, issued by the European Patent Office on Oct. 16, 2012 for related Application No. PCT/IB2012/053228.

\* cited by examiner

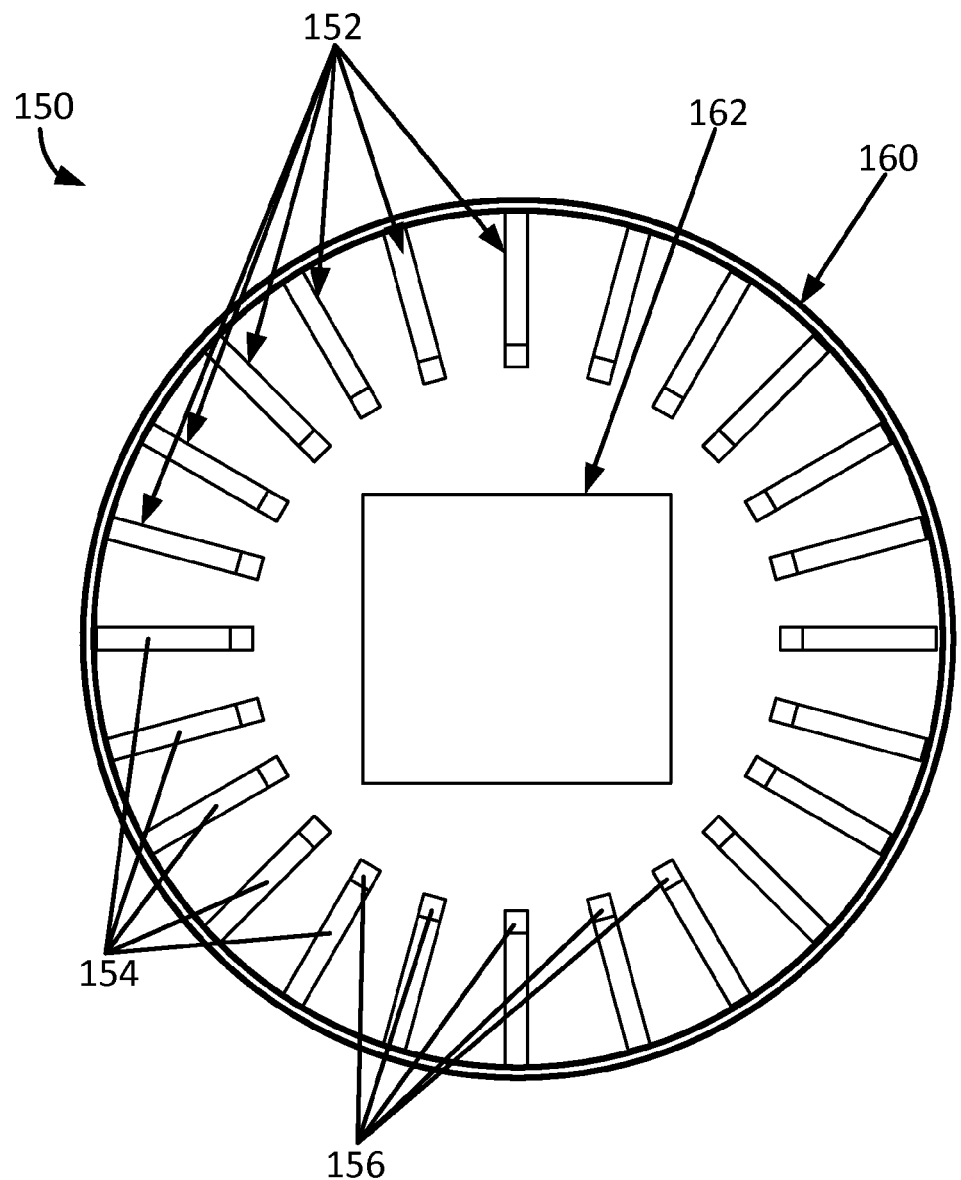

IMAGING USING PROBES

CROSS-REFERENCE TO RELATED APPLICATIONS

This application is the §371 U.S. National Stage of International Application No. PCT/IB2012/053228, filed 26 Jun. 2012, which claims the benefit of U.S. Provisional Application Ser. No. 61/503,783 filed 1 Jul. 2011, entitled "Imaging Using Probes," each of which are incorporated herein by reference in their entireties.

BACKGROUND

The present disclosure pertains generally to imaging systems and imaging methods, e.g., microwave and millimeter wave energy based imaging, using probes.

In the art of microwave tomography (MWT), an object of interest (OI) is illuminated by microwave energy and the scattered fields are collected outside the OI. The collected scattered fields may then be used to reconstruct qualitative, and possibly quantitative images, or interior maps, of the OI that include its location, geometry, shape, and dielectric properties. The ability to provide quantitative imaging and to utilize non-ionizing radiations associated with MWT make MWT a good candidate for use in many novel applications such as non-destructive testing in industrial applications, non-invasive imaging of biological tissues, remote sensing, geophysical survey of underground objects, and other security and military applications.

Due to the inherent non-linear and ill-posed behavior of the inverse scattering problem used in MWT, a substantial amount of electromagnetic scattering data may need to be collected in order to ensure a robust inversion and quantitatively-accurate image. The need for more data can be satisfied by several approaches such as, e.g., increasing the number of data acquisition points, using different frequencies, etc.

One advantageous approach to collect data for MWT may use co-resident antennas located at a region outside the OI, which may be referred to herein as a measurement domain. Each antenna may be successively activated as a transmitter to illuminate the OI from different angles. For each active transmitter, the electromagnetic field scattered by the OI, or the scattered field, is measured with the remaining antennas. The voltage measured by the receiving antennas may be used to infer the electromagnetic field impinging directly on each receiving antenna. This type of data collection approach may be referred to as a "direct" measurement approach.

A direct system 20 is illustrated in FIG. 15. As shown, an OI 10 is surrounded by a plurality of transmitting and receiving antennas 22. To image the OI, an antenna 22 (the leftmost antenna as shown) may deliver electromagnetic energy 12 (e.g., microwaves) having a selected polarization to the OI 10. The scattered field resulting from the electromagnetic energy impinging on the OI 10 may be collected by one or more of the antennas 22 that are not delivering electromagnetic energy to the OI 10 (e.g., all the antennas 22 except for the leftmost antenna, etc.). The signals received by the antennas 22 may be used to reconstruct an image of the OI within a pre-defined imaging domain 32.

The measurement domain 30 may not be precisely determined because all fields around the antennas 22 may contribute to the received voltage. Further, as described, all polarizations of the electromagnetic energy delivered by the transmitting antenna 22 may contribute to the voltage received by each of the receiving antennas 22 of this exemplary direct system 20.

SUMMARY

One exemplary method of imaging an object using microwave tomography includes providing a plurality of antenna assemblies (e.g., three or more antenna assemblies, etc.) positioned about an object (e.g., the plurality of antenna assemblies may be positioned around a perimeter of the object and lie in a plane). Each antenna assembly of the plurality of antenna assemblies may include an antenna and one or more probes (e.g., two or more probes, etc.) spatially distributed relative to the antenna. Each probe of the one or more probes may be configurable in an active state and an inactive state. Each probe may interact with electromagnetic energy when in the active state and may be nonresponsive to electromagnetic energy when in the inactive state. The exemplary method may further include individually configuring each probe of the one or more probes of the plurality of antenna assemblies in the active state while configuring the remaining probes of the one or more probes of the plurality of antenna assemblies in the inactive state until each probe of the one or more probes of the plurality of antenna assemblies has been individually configured in the active state, delivering electromagnetic energy using the antenna of at least one antenna assembly of the plurality of antenna assemblies to irradiate the object resulting in scattered electromagnetic energy for each probe being configured in the active state, sampling the scattered electromagnetic energy using the antenna of at least one antenna assembly of the plurality of antenna assemblies for each probe being configured in the active state, and reconstructing an image (e.g., a quantitative image) of the object based on the sampled scattered electromagnetic energy.

One exemplary system for use in imaging an object using microwave tomography includes a plurality of antenna assemblies positionable (e.g., three or more antenna assemblies, etc.) about an object (e.g., the plurality of antenna assemblies may be positioned around a perimeter of the object and lie in a plane). Each antenna assembly of the plurality of antenna assemblies may include an antenna configured to deliver electromagnetic energy to irradiate the object resulting in scattered electromagnetic energy and to sample scattered electromagnetic energy and one or more probes (e.g., two or more probes, etc.) spatially distributed relative to the antenna. Each probe of the one or more probes may be configurable in an active state and an inactive state. Each probe may interact with electromagnetic energy when in the active state and each probe may be nonresponsive to electromagnetic energy when in the inactive state. The exemplary system further includes processing apparatus coupled to the plurality of antenna assemblies. The processing apparatus may be configured to individually configure each probe of the one or more probes of the plurality of antenna assemblies in the active state while configuring the remaining probes of the one or more probes of the plurality of antenna assemblies in the inactive state until each probe of the one or more probes of the plurality of antenna assemblies has been individually configured in the active state and initiate the delivery of electromagnetic energy using the antenna of at least one antenna assembly of the plurality of antenna assemblies to irradiate the object resulting in scattered electromagnetic energy for each probe being configured in the active state. The processing apparatus may be further configured to initiate the sampling of the scattered electromagnetic energy using the antenna of at least one antenna assembly of the plurality of antenna assemblies for each probe being configured in the active state and reconstruct an image (e.g., a quantitative image) of the object based on the sampled scattered electromagnetic energy.

In one or more exemplary methods and systems, the one or more probes may include a first probe configured to interact with electromagnetic energy of a first selected polarity when in the active state and a second probe configured to interact with electromagnetic energy of a second selected polarity when in the active state. In at least one embodiment, the first selected polarity is different than the second selected polarity (e.g., the first selected polarity may be perpendicular to the second selected polarity). In at least one embodiment, delivering electromagnetic energy using the antenna of the at least one antenna assembly of the plurality of antenna assemblies to irradiate the object may include delivering electromagnetic energy at a slant polarity. An exemplary slant polarity may include components of the first selected polarity and the second selected polarity.

In one or more exemplary methods and systems, each antenna assembly of the plurality of antenna assemblies is in a fixed position relative to the object. In at least one embodiment, one or more of the plurality of antenna assemblies are configured to be attached to the object. Further, in at least one embodiment, the antenna and the one or more probes of each antenna assembly of the plurality of antenna assemblies are stationary with respect to each other.

In one or more exemplary methods and systems, delivering electromagnetic energy using the antenna of at least one antenna assembly of the plurality of antenna assemblies to irradiate the object resulting in scattered electromagnetic energy may include individually delivering electromagnetic energy with the antenna of each antenna assembly of the plurality of antenna assemblies until the antenna of each antenna assembly has individually delivered electromagnetic energy. Further, in one or more exemplary methods and systems, sampling the scattered electromagnetic energy using the antenna of at least one antenna assembly of the plurality of antenna assemblies may further include sampling the scattered electromagnetic energy using the antenna of the antenna assembly of the plurality of antenna assemblies that includes the probe configured in the active state. Still further, in one or more exemplary methods and systems, sampling the scattered electromagnetic energy using the antenna of at least one antenna assembly of the plurality of antenna assemblies further may include sampling the scattered electromagnetic energy using the antennas of two or more antenna assemblies of the plurality of antenna assemblies. In at least one embodiment, the sampled scattered electromagnetic energy using the antennas of two or more antenna assemblies of the plurality of antenna assemblies may be combined in analog.

In one or more exemplary methods and systems, each probe of the one or more probes of the plurality of antenna assemblies conductive segments may include a plurality of conductive segments and a plurality of switchable segments coupling the conductive segments. The switchable segments may be configurable between a conducting configuration and a non-conducting configuration. The plurality of conductive segments may be electrically coupled via the switchable segments when the switchable segments are configured in the conducting configuration, and the plurality of conductive segments may be electrically isolated from one another when the switchable segments are configured in the non-conducting configuration. Further, the switchable segments may be configured in the conducting configuration when the probe is in the active configuration, and the switchable segments may be configured in the non-conducting configuration when the probe is in the inactive configuration.

In one or more exemplary methods and systems, sampling is also performed by the antenna of each antenna assembly of the plurality of antenna assemblies when all the probes of the plurality of probes are configured in the inactive state to establish a baseline measurement for the antenna of each antenna assembly.

Exemplary imaging systems and methods described herein may provide an imaging modality that illuminates an object of interest (OI) by microwave or millimeter wave electromagnetic energy with multiple polarizations simultaneously. A multitude of antennas (e.g., collecting or receiving antennas, transmitting antennas, etc.) and probes may be introduced, which may be distributed at different spatial locations around the OI. Due to the spatial distribution of antennas, the OI may be illuminated from different angles. The probes may be parallel to different polarizations. The probes may then be activated/modulated successively to interact with the field without mechanically rotating the system for collecting different polarizations.

Each activated probe may generate a signal, which may be measured by the nearest antenna. This signal and the location of probe may be recorded by processing apparatus, which may use such data to reconstruct a quantitative and qualitative image of the object. During the measurement, inactive probes may be kept "invisible" from the microwave energy. For efficient invisibility and sensitive modulation, a number of switching elements may be embedded along the axis of each probe. In one or more embodiments, the probe may not be a printed wire and/or may have a more sophisticated geometry (e.g., no lying along an axis).

In other words, an OI may be simultaneously illuminated by different polarizations of microwave energy. The scattered field may then be collected at one or more locations outside the object being imaged using scattering probes. More specifically, different polarizations may be collected using the scattering probes and a multitude of collector antennas without any mechanical movement. The probes and antennas may be distributed in various spatial regions and may scan different polarizations very quickly, e.g., due to no mechanical movement. Further, processing apparatus may record the collected fields and reconstruct quantitative and qualitative images of the object.

One exemplary imaging system may include a multitude of antennas and a multitude of probes (e.g., the antennas and the probes may be distributed at different selected, or arbitrary, spatial locations including a three dimensional imaging system). Each of the antennas may be equipped with a multitude of probes and each of the antennas can act as either a transmitter with multiple angles of illumination (e.g., transmitting microwave energy that may contain at least dual polarizations) or a collector. The multitude of probes may be distributed at numerous spatial locations along arbitrary polarizations. Further, the exemplary imaging system may utilize a data acquisition method that includes switching of both high frequency antennas and low frequency probe modulation. Generally, one exemplary imaging system may be described as a portable microwave tomography system, which encircles the object to be imaged and captures different polarizations.

In one or more exemplary imaging systems and methods, the probes may include an optimum, or optimal, amount of PIN diodes in series for use to activate or inactivate the probes. The number and the location of PIN diodes may be calculated through an optimization procedure using a combination of full wave simulation and the circuit behavior of the switching diode. The diodes may be electrically or optically driven (e.g., electrically or optically activated/inactivated).

One or more exemplary imaging systems and methods described herein may be single-polarized, dual-polarized, or multi-polarized. For example, in one or more exemplary imaging systems and methods, a single-polarized configuration for vertical polarization may be implemented using broadband antennas, such as Vivaldi antennas, that operate in wide-frequency imaging systems. Further, for example, a dual-polarized configuration may be configured for use with vertical and horizontal polarizations, which may be implemented by simultaneous illumination of both polarizations using slanted horn antennas. In such a dual-polarized configuration, the vertical and horizontal electromagnetic scattered fields may be collected separately without any mechanical rotation or movement. Still further, biasing circuitry of each probe may be designed so as to minimize the interference of biasing wires (e.g., wires electrically coupled to each probe to activate or inactivate the probe).

In one or more exemplary imaging systems and methods, at least a portion of the system or imaging setup may be similar to a belt and be attached to an object of interest. For example, the antennas and probes may be coupled to the belt.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 4B is a top view of the imaging setup of FIG. 4A.

DETAILED DESCRIPTION OF EXEMPLARY EMBODIMENTS

Figure 1:
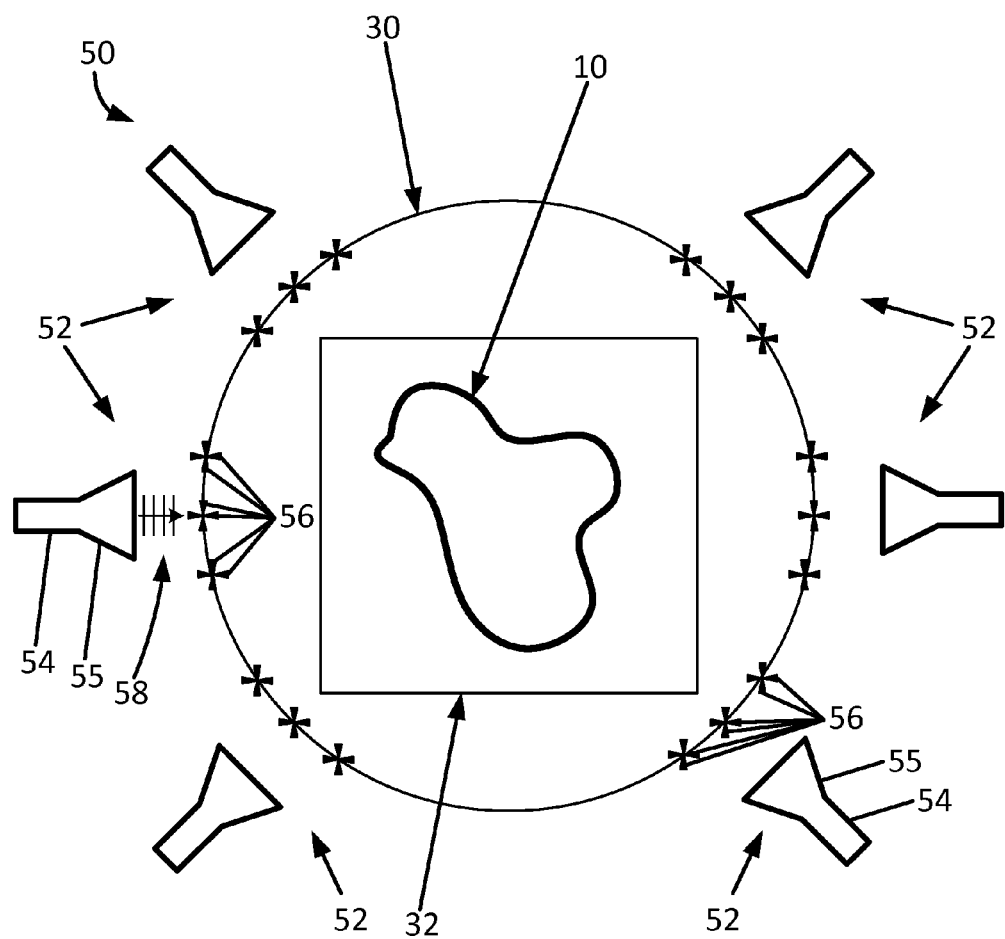
FIG. 1 is a plan view of an exemplary imaging setup.

An alternative approach to "direct" data collection in microwave tomography is to utilize an "indirect" data collection method. Systems using an indirect data collection method may use a number of scattering probes located at a relatively close distance to a receiver, or collector, antenna (e.g., such scattering probes may be described as being closely coupled or associated with a receiver antenna). The data collection may be performed while a transmitter antenna illuminates the OI. The scattering probes may then be sequentially modulated to interact with the field at their locations. Due to these interactions between the probes and the scattered field, a scattering signal may be produced, which is proportional to the field at the probe's location, and may be detected by one or more receiver antennas (e.g., the receiver antenna closest to the probe being modulated is used to detect the signal). Since the electrical activity at the probe is not directly measured or sampled, but the scattered field affected and unaffected by the probe is measured and then compared to determine the electromagnetic field at the probe location, it may be described that the electromagnetic field at the probe is "inferred." Using these measurements, one polarization of the electromagnetic field at the scattering probe's location may be inferred. This technique may be generally referred to as the Modulated Scatterer Technique (MST).

Indirect systems, however, may not scan the entire spatial periphery around the object, and often only collect a single polarization of the scattered electromagnetic field, unless the probes are mechanically rotated. For example, the probes of an indirect system often lie in a plane. Thus, the polarization advantage of the microwave tomography (MWT) may not be fully utilized (e.g., polarization is a unique aspect of MWT due to the vectorial properties of electromagnetic fields, which is not available in many other imaging modalities), and therefore, reconstructed images using an indirect system may not provide sufficient resolution. Further, transmitter antennas in indirect systems may often not be used for data collection, and in some cases, the indirect imaging algorithms may not generate a quantitative image.

Microwave imaging techniques have been described in U.S. Pat. No. 5,051,748 to Pichot et al.; U.S. Pat. No. 5,430,369 to Bolomey et al. and U.S. Pat. No. 7,746,266 to Zoughi et al., each of which are incorporated herein in their entireties.

As described herein, at least two different approaches exist for data collection in microwave tomography: a direct method and; an indirect method. The direct approach may suffer from certain drawbacks. Further, the need for a high density of measurement points may conflict with another important design consideration that is the need for a sufficiently large spatial separation of the collector antennas in order to minimize mutual coupling between antennas.

Moreover, when all polarizations of the impinging fields contribute to the received voltage, it may be difficult to relate the measured voltage to a single polarization. Thus, a unique potential advantage of MWT over other modalities may be lost, which may be overcome (e.g., to some extent) through the use of single-polarization probes with small cross-polarization sensitivity (which may be difficult in a near-field environment). Using single-polarization probes, measurement of the different polarizations may request the rotation of such probes and the antenna elements.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, apparatus, and systems shall be described with reference to FIGS. 1-14. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

An exemplary imaging setup 50, or configuration, is depicted in FIG. 1. The imaging setup 50 includes a plurality antenna assemblies 52 positioned about an object of interest 10. For example, the plurality of antenna assemblies 52 may be positioned completely around the object of interest 10. Further, for example, the plurality of antenna assemblies 52 may be positioned partially around the object of interest 10 such as one quarter around the OI 10, halfway around the OI 10, three quarters around the OI 10, etc. The exemplary imaging setups described herein may include any number of antenna assemblies such as, e.g., 2 or more antenna assemblies, 3 or more antenna assemblies, 5 or more antenna assemblies, 6 or more antenna assemblies, 7 or more antenna assemblies, 10 or more antenna assemblies, 12 or more antenna assemblies, 16 or more antenna assemblies, 24 or more antenna assemblies, 50 or less antenna assemblies, 40 or less antenna assemblies, 36 or less antenna assemblies, 30 or less antenna assemblies, 24 or less antenna assemblies, 18 or less antenna assemblies, 16 or less antenna assemblies, 8 or less antenna assemblies, etc.

As shown in FIG. 1, the exemplary imaging setup 50 includes 6 antenna assemblies 52 spaced about the object of interest 10 defining a measurement domain 30. The measurement domain 30 may be defined as the area within an electromagnetic scattered field created by the imaging setup 50 within which data may be gathered using the imaging setup 50. Further, the imaging setup 50 may be configured to image an imaging domain 32 containing the object 10 located within the measurement domain 30. The imaging domain 32 may be a subset, or portion, of the measurement domain 30.

The antenna assemblies 52 of the imaging setup 50 may be located about the object 10 in any spacing and/or distance from the object 10 so as to be able to provide scattering data useful for the reconstruction of an image of the object 10. The antenna assemblies 52 may be in a fixed position relative to each other and/or to the object 10 during imaging such that the position of the antenna assemblies does not change during imaging. For example, the antenna assemblies 52 may be attached to a structure such as a measurement chamber within which the object 10 may be located. In at least one embodiment, the antenna assemblies 52 may be positioned around a perimeter of the object and lie in a plane.

Further, for example, the antenna assemblies 52 may be attached to the object 10 itself. In at least one embodiment, the antenna assemblies 52 may be attached to a belt-like apparatus that may be wrapped around the object 10.

To provide useful scattering data for reconstruction of an image of the object 10, the positions, or locations, of the antenna assemblies 52 with respect to each other must be known or determined. When the antenna assemblies 52 are attached to a structure, the positions of the antenna assemblies 52 and portions are already known (e.g., due to being fixed to the structure). When the antenna assemblies 52 are not attached to a structure, and instead attached to the object 10 itself or not-fixedly arranged prior to imaging, a calibration procedure may be executed to determine the positions/locations of the antenna assemblies prior to imaging as described further herein.

As shown in FIG. 1, the antenna assemblies 52 are located equidistantly from the center of the imaging domain 32 but are not spaced equidistantly from each other. In other embodiments, the antenna assemblies 52 may be spaced equidistantly from each other.

Each exemplary antenna assembly 52 may include an antenna 54 and one or more probes 56 associated with each antenna 54 (e.g., the one or more probes 56 associated with an antenna 54 may be in the vicinity of such antenna 54). Each antenna assembly 52 may further include a waveguide 55 configured to collect and direct electromagnetic energy towards the antenna 54. Each antenna 54 may be used as a transmitter of electromagnetic energy (e.g., microwave energy) and/or a receiver of electromagnetic energy (e.g., scattered microwave energy). Each probe 56 may be configured to interact with a selected polarity of electromagnetic energy. In at least one embodiment, all of the probes 56 may be configured to interact with the same selected polarity. In at least one embodiment, two or more groups of probes 56 may be configured to interact with two or more different selected polarities, respectively.

For example, as shown, six probes 56 are spatially distributed relative to each antenna 54 about the measurement domain 30 (e.g., on the circumference of the measurement domain 30). Three probes 56 of each antenna assembly 52 may be oriented horizontally and the remaining three probes may be oriented vertically, e.g., to interact with horizontal and vertical polarizations, respectively, as described further herein. The horizontal polarization is perpendicular to the vertical polarization. Further, the probes 56 may include biasing circuitry and may be designed to reduce cross-polarization sensitivity so as to only interact with a single polarization.

A probe 56 may be described as being closely coupled to the nearest antenna 54, which may be the best antenna for measuring the signal from the closely-coupled probe. Although six probes 56 are associated with each antenna 54 in the antenna assemblies 52 shown in FIG. 1, exemplary antenna assemblies may include any number of probes associated with (e.g., closely coupled to) each antenna such as, e.g., 2 or more probes, 3 or more probes, 4 or more probes, 5 or more probes, 6 or more probes, 8 or more probes, 10 or more probes, 15 or more probes, 30 or less probes, 25 or less probes, 20 or less probes, 15 or less probes, 12 or less probes, 10 or less probes, 8 or less probes, 5 or less probes, etc.

Each probe 56 may be configured in an active state or an inactive state. When in the active state, a probe 56 may interact with electromagnetic energy (e.g., the electromagnetic energy being used for imaging such as microwaves) and, when in an inactive state, a probe 56 is nonresponsive to electromagnetic energy as will be described further herein. While electromagnetic energy 58 is being transmitted, or delivered, by an antenna 54, one probe 56 may be activated, or modulated, to infer the scattered electromagnetic field at that probe 56 while the remaining probes 56 may be kept inactive, or "invisible," from the scattered field.

As shown, the leftmost antenna 54 may transmit electromagnetic energy 58 of a selected polarity to the object of interest 10 (OI) within a measurement domain 30 resulting in a scattered field. In one or more embodiments, the transmitting antenna 54 may radiate a selected polarization, which may include a single polarization or a combination of multiple polarizations. In at least one embodiment, a circular polarization may be transmitted, or delivered, by the transmitting antenna 54. In this embodiment, the measurement domain 30 may be precisely determined because the locations of antenna assemblies 52 are known, and therefore, the locations of the antennas 54 and the probes 56, may be known.

To establish a baseline measurement for the imaging setup 50, sampling may be performed using one or more antennas 54 of each antenna assembly 52 individually when all the probes of the plurality of probes 56 are configured in the inactive state. Such baseline measurements for the antenna 54 of each antenna assembly 52 may be used as calibration data, e.g., for comparison to the sampled scattered field collected when at least one probe 56 is active.

Figure 2:
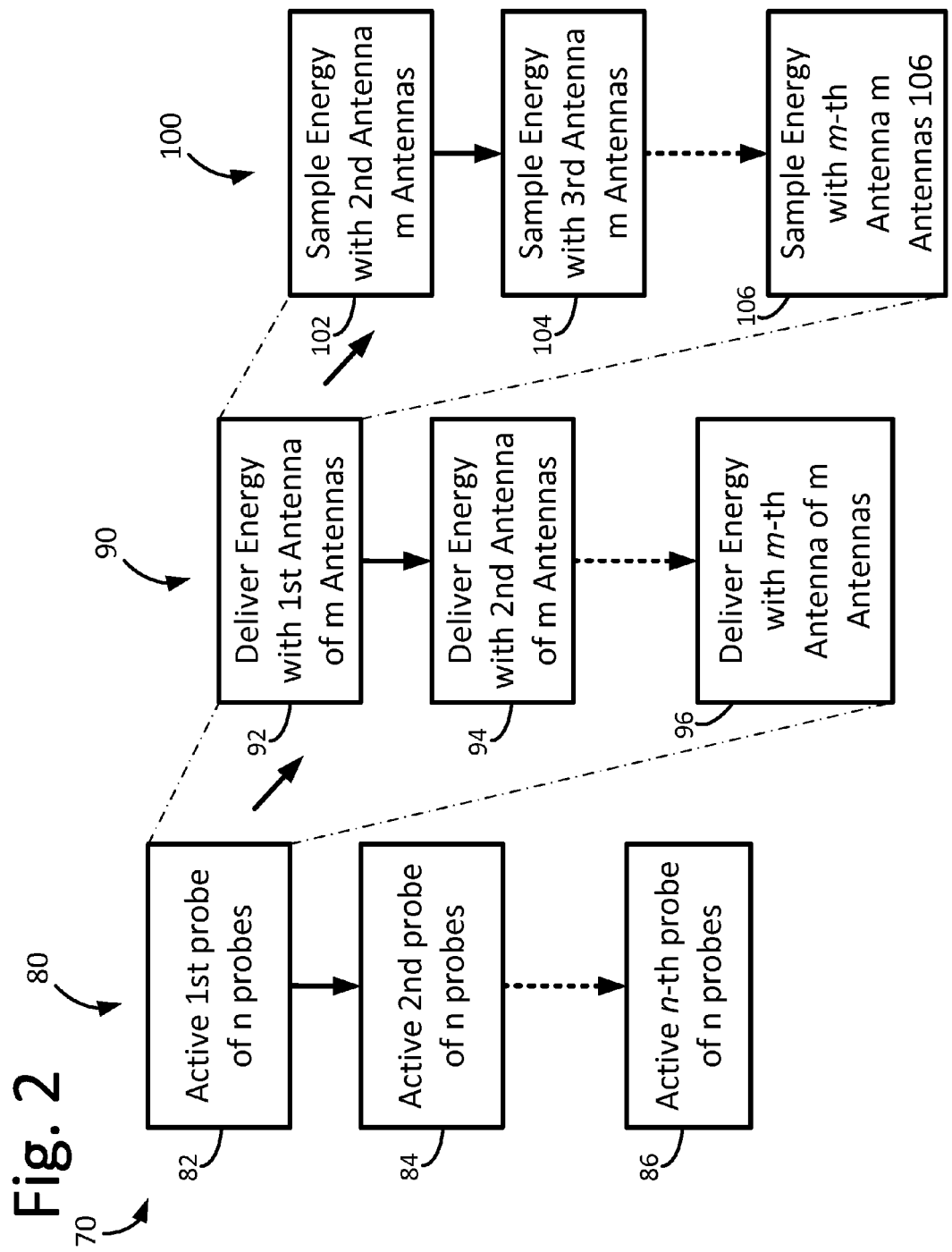
FIG. 2 is a flow diagram for an exemplary imaging method, e.g., for use with the imaging setup of FIG. 1.

An exemplary method 70 of imaging using the system of FIG. 1 is depicted in FIG. 2. The exemplary method 70 includes configuring each probe individually in the active state 80, delivering electromagnetic using at least one antenna to irradiate an object of interest resulting in a scattered field for each active probe 90, and sampling the scattered field using at least one antenna for each active probe and each antenna delivering electromagnetic energy 100. In other words, each probe may interact with each scattered field created by a different antenna delivering electromagnetic energy and the resultant scattered field may be measured or sampled. The antenna closely coupled to the activated probe may be used to sample, or measure, the electromagnetic energy for the activated probe, or one or more antennas may be used to sample the electromagnetic energy for the activated probe. Although exemplary method 70 has a particular sequence starting with activating one probe at a time, and then delivering and sampling electromagnetic energy for each probe being active one a time, it is to be contemplated that different sequences may be used to perform the exemplary methods described herein. For example, instead of starting with each probe being active, an exemplary method may begin by delivering electromagnetic energy with one antenna while the probes may be sequentially activated one at a time and the resultant electromagnetic field may be measured using at least one antenna.

One probe may be activated to interact with the electromagnetic energy to be delivered by the antennas while the remaining probes are invisible to the electromagnetic energy 80. As such, as shown in FIG. 2, a first probe of n probes may be activated while the remaining probes are inactive 82 (e.g., such that the active first probe may be used in the sampling of the scattered field resulting from delivering energy to the OI 10), and a second probe of n probes may be activated while the remaining probes are inactive 84 (e.g., such that the active second probe may be used in the sampling of the scattered field resulting from delivering energy to the OI 10). The method 70 may continue activating each probe of n probes until the n-th probe has been activated 86.

For each probe being active, electromagnetic energy may be delivered using at least one antenna of m antennas to irradiate an object of interest resulting in scattered electromagnetic energy or a scattered field 90. The electromagnetic energy may be delivered using a single antenna or a combination of antennas. Further, various antenna configurations (e.g., changing over time) may be used to deliver electromagnetic energy. In the embodiment depicted in FIG. 2, one antenna individually delivers electromagnetic energy to the object at a time, or sequentially, until each of the antennas has individually delivered electromagnetic energy to the object (e.g., each of the antennas may sequentially deliver electromagnetic energy to the object). For example, a first antenna of m antennas may deliver electromagnetic energy to the object 92 for the first probe of n probes being active 82, and then a second antenna of m antennas may deliver electromagnetic energy to the object 94 for the first probe of n probes being active 82. The method 70 may continue delivering electromagnetic energy with each antenna of m antennas until the m-th antenna has delivered electromagnetic energy to the object 96.

For each antenna delivering electromagnetic energy to the object, the electromagnetic energy may be sampled, or measured, using at least one antenna of m antennas that is not being used to deliver electromagnetic energy 100. The electromagnetic energy may be sampled, or measured, using a single antenna and/or multiple antennas. In at least one embodiment (e.g., in the example described herein with respect to FIGS. 9-14), only the antenna closely coupled to the activated probe may be used to sample the scattered electromagnetic field (e.g., since sampling with more than one antenna for each probe being activated may be redundant). When using multiple antennas, the signals may be combined (e.g., in analog) into a single signal or each signal may be used discretely.

In the embodiment, depicted in FIG. 2, one antenna individually samples electromagnetic energy (e.g., the scattered field, or scatted electromagnetic energy, resulting from the delivery of electromagnetic energy to the object) at a time, or sequentially, until each of the antennas has individually sampled the electromagnetic energy for that particular probe and transmitting antenna configuration. For example, a second antenna of m antennas (e.g., the second antenna may be used since the first antenna is being used to deliver the electromagnetic energy to the object) may sample electromagnetic energy 102 for the first probe of n probes being active 82 and for the first antenna delivering electromagnetic energy to the object 92, and then a third antenna of in antennas may sample electromagnetic energy 104 for the first probe of n probes being active 82 and for the first antenna delivering electromagnetic energy to the object 92. The method 70 may continue sampling electromagnetic energy with each antenna of m antennas until the m-th antenna has sampled electromagnetic energy 106 for the first probe of n probes being active 82 and for the first antenna of m antennas delivering electromagnetic energy to the object 92.

After each of m antennas has sampled the scattered field 100 for the first probe of n probes being active 82 and for the first antenna delivering electromagnetic energy to the object 92, the method 70 may deliver electromagnetic energy using the second antenna 94 to the object 10 for the first probe of n probes being active 82 and then sample the scattered field using each of m antennas 100. Likewise, after each of m antennas has delivered electromagnetic energy to the object 90 for the first probe of n probes being active 82 (such that the resultant field may be sampled 100), the method 70 may activate the second probe of n probes 84 and may further deliver electromagnetic energy to the object 90 such that the resultant scattered field 100 may be sampled.

Using the exemplary method 70 depicted in FIG. 2, many scattered field data sets, or imaging data sets, may be gathered for each probe from multiple different angles. Such data sets may be used to reconstruct an image of the object.

As described herein, although the method 70 delivers electromagnetic energy using a single antenna at a time, or individually, the exemplary methods and/or systems described herein may deliver electromagnetic energy using more than one antenna. For example, multiple combinations of antennas may be used to deliver electromagnetic energy to the object to provide additional scattered field data. Likewise, although the exemplary method 70 samples electromagnetic energy using a single antenna at a time, or individually, the exemplary methods and/or systems described herein may sample electromagnetic energy using more than one antenna. In essence, different unique combinations of antennas may be used to deliver and/or sample electromagnetic energy.

For example, the signals measured from multiple antennas at the same time could be combined in analog (e.g., using analog circuitry). When the separation between the probes and their closely-coupled antenna increases, the antenna becomes less sensitive to changes of the probe. Thus, multiple antennas may be then connected to a power-combiner through parallel transmission lines, and routed to a single port.

As before, the scattered field is being measured at the active probe location, and the probe may interact with one or more of the combined, multiple collector antennas. Although a collector antenna closer to the probe may measure, or pick up, more power than a collector antenna in a farther distance, the combined power may deliver the interaction between the probe and all the collectors, and thus, the sensitivity may increase.

As described herein, the exemplary system 50 may use the antenna assemblies 52 to deliver electromagnetic energy to (e.g., to illuminate) the OI 10 from multiple different angles and to sample the resultant scattered field from multiple different angles. The data gathered may then be processed using a processing apparatus to reconstruct a quantitative image of the OI 10 in an imaging domain 32. As used herein, a "quantitative" image may be defined as an image that includes data that is calibrated to directly relate to an actual property such as dielectric permittivity. For instance, a person having skill in the art may determine the permittivity of a particular location in an object based on the quantitative image. In other words, the data in a quantitative image is not data that is merely relative to itself.

Implementing such a data-collection apparatus within a microwave tomography (MWT) system for generating quantitative images may allow for many possible diversities of field interrogation and measurement: the use of multiple frequencies, the collection of substantial amounts of scattering data at the multitude of probe locations, the use and measurement of arbitrary polarizations (without any need for mechanical rotation for fast data acquisition), and the use of a multitude of transmitter locations to introduce a multitude of incident fields upon the OI 10.

Figure 3:
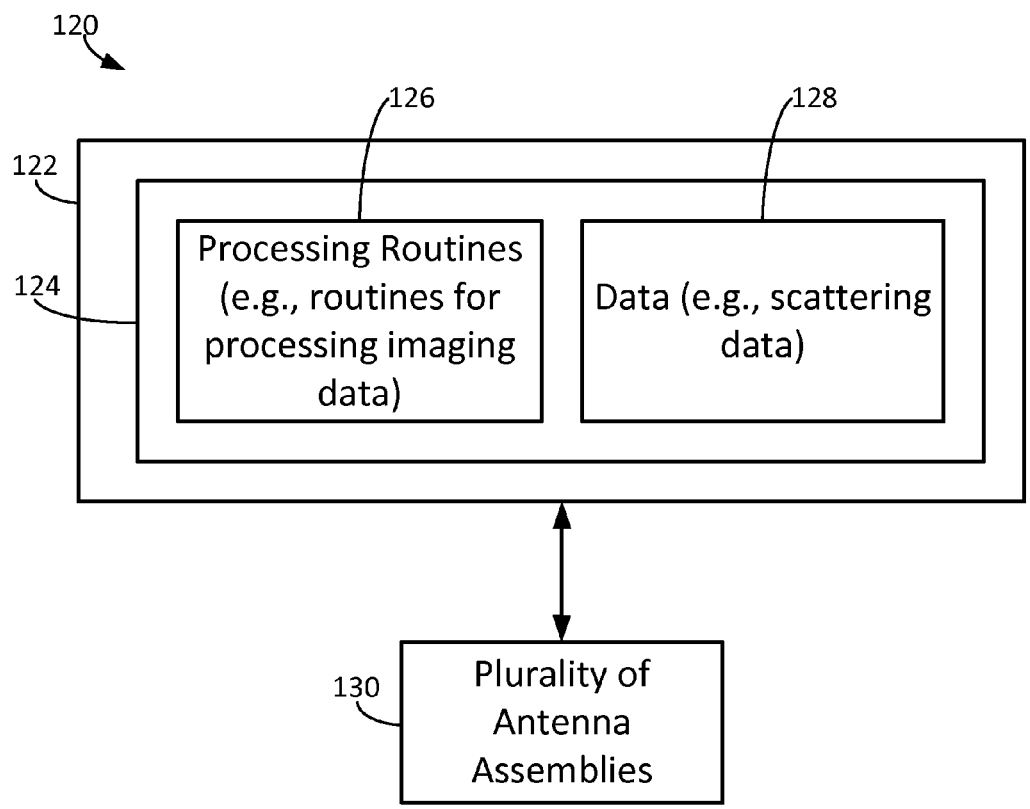
FIG. 3 is a block diagram of an exemplary imaging system, e.g., for use with the imaging setup of FIG. 1.

An exemplary imaging system 120 (e.g., a MWT imaging system), e.g., for use with the imaging setup of FIG. 1 and the method of FIG. 2, is depicted in FIG. 3. The system 120 may include processing apparatus 122 and a plurality of antenna assemblies 130 (e.g., the antenna assemblies 52 of imaging setup 50). The processing apparatus 122 may be operably coupled to the plurality of antenna assemblies 130 to facilitate imaging of an object of interest using the plurality of antenna assemblies 130. Generally, the processing apparatus 122 may control the image data acquisition using the plurality of antenna assemblies 130 and may perform the image reconstruction. More specifically, the processing apparatus 122 may be configured to control and/or initiate the functionality of the plurality of antenna assemblies 130 for use in imaging an object. For example, the processing apparatus 122 may configure one or more probes of the plurality of antenna assemblies 130 in an active or inactive state. Further, for example, the processing apparatus 122 may initiate the delivery of electromagnetic energy using one or more antennas of the plurality of antenna assemblies 130. Still further, for example, the processing apparatus 122 may initiate the sampling of electromagnetic energy using one or more antennas of the plurality of antenna assemblies 130.

Further, the processing apparatus 122 includes data storage 124. Data storage 124 allows for access to processing programs or routines 126 and one or more other types of data 128 that may be employed to carry out the exemplary imaging methods (e.g., one which is shown generally in the block diagram of FIG. 2).

For example, processing programs or routines 126 may include programs or routines for performing computational mathematics, matrix mathematics, compression algorithms (e.g., data compression algorithms), calibration algorithms, image construction algorithms, inversion algorithms, signal processing algorithms, standardization algorithms, comparison algorithms, vector mathematics, or any other processing required to implement one or more embodiments as described herein.

Data 128 may include, for example, sampled electromagnetic energy (e.g., sampled or collected using the plurality of antenna assemblies 130), data representative of measurements (e.g., electromagnetic scattering data), results from one or more processing programs or routines employed according to the disclosure herein (e.g., reconstructed images of an object of interest), or any other data that may be necessary for carrying out the one or more processes or methods described herein.

In one or more embodiments, the system 120 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The program used to implement the processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the system 120 may be implemented using a computer readable storage medium, configured with a computer program, where the storage medium so configured causes the computer to operate in a specific and predefined manner to perform functions described herein.

Likewise, the imaging system 120 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data).

The processing apparatus 122 may be, for example, any fixed or mobile computer system (e.g., a personal computer or mini computer). The exact configuration of the computing apparatus is not limiting and essentially any device capable of providing suitable computing capabilities and control capabilities (e.g., control the imaging set up configuration and acquire data, such as electromagnetic scattering data) may be used. Further, various peripheral devices, such as a computer display, mouse, keyboard, memory, printer, scanner, etc. are contemplated to be used in combination with the processing apparatus 122.

Further, in one or more embodiments, the output (e.g., an image, image data, scattered field data, an image data file, a digital file, a file in user-readable format, etc.) may be analyzed by a user, used by another machine that provides output based thereon, etc.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus 124 described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing computational mathematics (e.g., matrix inversions, substitutions, Fourier transform techniques, etc.) to reconstruct the images described herein (e.g., from sampled electromagnetic scattering data).

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information.

The methods described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, image processing devices, or other devices. The term "processing apparatus," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

In one or more embodiments, the exemplary system 120 may further include a probe driver circuit operably coupled between the plurality of antenna assemblies 130 and the processing apparatus 122. The probe driver circuit may be used to activate a specific probe in a certain location and polarization upon a request from the processing apparatus 122. In at least one embodiment, the probe driver circuit may be connected via USB connection to the processing apparatus 122. Further, the connection of the probe driver circuit unit and the probes may be established using a pair of biasing wires for each probe. The exemplary system 120 may further include a measurement chamber containing the plurality of antenna assemblies 130.

In one or more embodiments, the exemplary system 120 may further include a Vector Network Analyzer (VNA) unit or a coherent detect unit (e.g., implementing a modulation scheme) employed to capture the signals received by the antennas of the plurality of antenna assemblies 130 for the processing apparatus 122. Due to the presence of multiple antennas, an RF multiplexer unit may be employed by the system 120 to connect the antennas of the plurality of antenna assemblies 130 to the VNA unit. The connections between the RF multiplexer and the VNA and the RF multiplexer to the plurality of antenna assemblies 130 may be established by RF cables. In at least one embodiment, the processing apparatus 122 may be connected to the VNA and the RF multiplexer via General Purpose Interface Bus (GPIB) connections. Upon activation of a probe, one or more antennas (e.g., an antenna closely coupled to the activated probe) may be switched, or connected, through the multiplexer unit to receive scattering data.

Figure 4A:
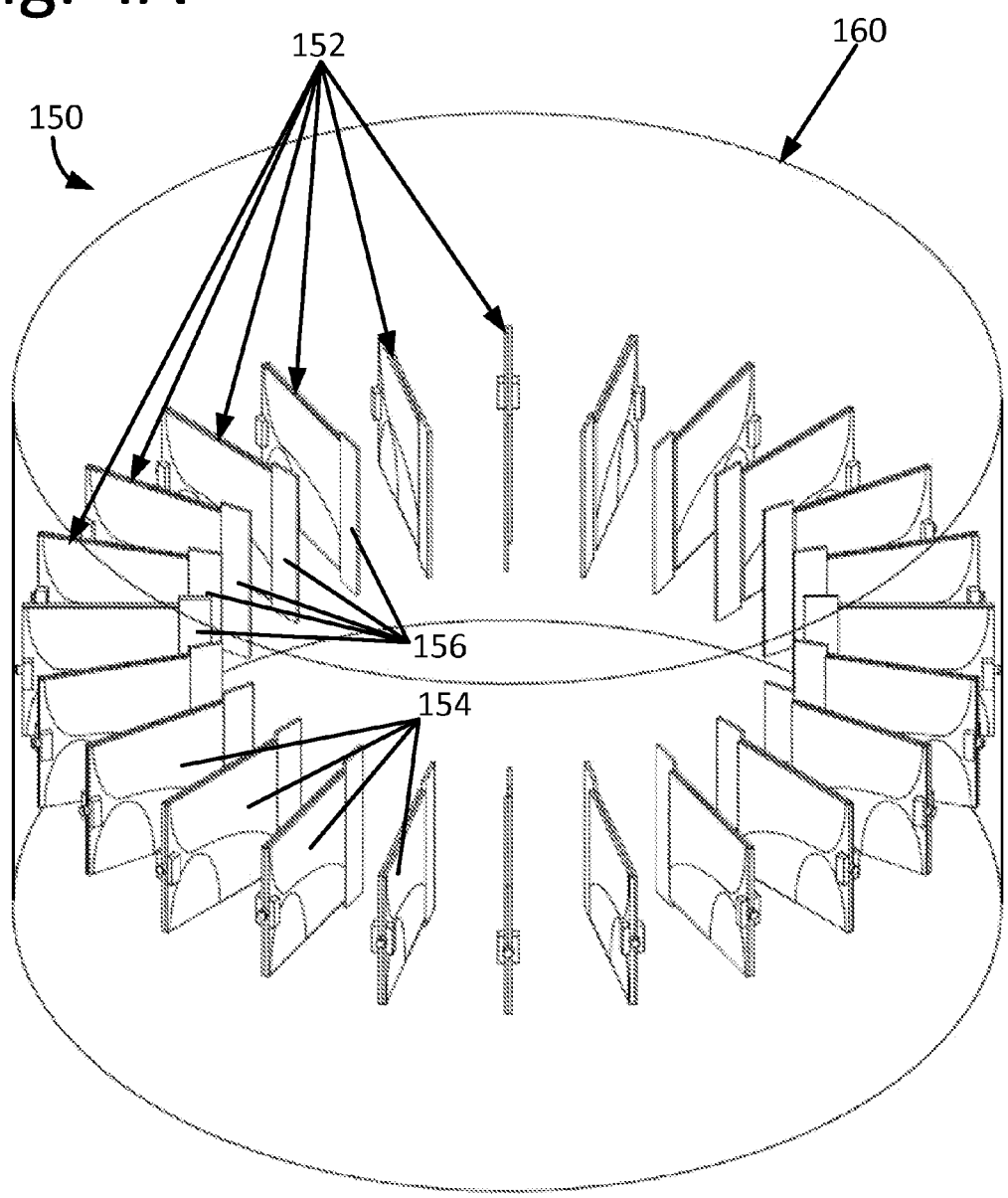
FIG. 4A is a perspective view of an exemplary single-polarized imaging setup.

An exemplary imaging setup 150 for use with single polarized microwaves is depicted in FIGS. 4A-4B. The exemplary setup 150 includes a plurality of antenna assemblies 152, each including an antenna 154 and a probe 156. The antennas 154 are Double Layered Vivaldi Antennas (DLVA) and the probes 156 are dipole wires. The probes 156 are fixedly positioned in front of each antenna 154 for near-field measurement and are used to measure only the vertical polarization (also known as the Transverse Magnetic (TM) case).

The antenna assemblies 152 of the imaging setup 150 may be positioned about an object of interest (e.g., positioned entirely around, position partially around, etc.) and configured to image an image domain 162. In other words, the antenna assemblies for use in the exemplary systems and methods may be distributed about an object of interest to provide a plurality of unique electromagnetic scattering data sets to be used to reconstruct an image of the object. For example, as shown in each of the FIG. 1 and FIGS. 4A-4B, the antenna assemblies 52, 152 are configured to surround an object of interest in a circular configuration.

Figure 5A:
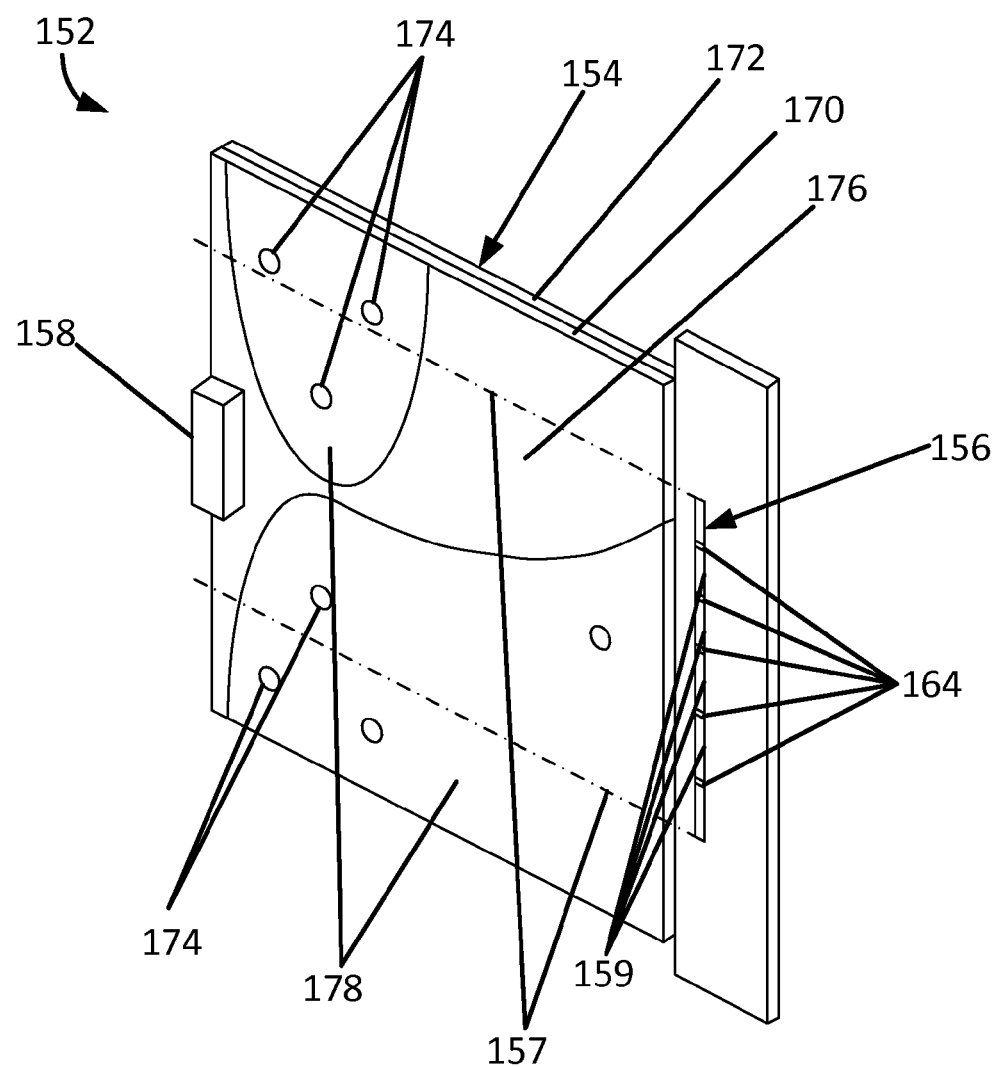
FIG. 5A is perspective view of an exemplary antenna assembly of the imaging setup of FIG. 4.

The imaging setup 150 of FIGS. 4A-4B may further include a measurement chamber 160, e.g., that may be formed of PLEXIGLAS® material. As shown, twenty-four antenna assemblies 152 (i.e., twenty-four antennas 154 and twenty-four probes 156) are mounted in this chamber 160. A more detailed view of an antenna assembly 152 including an antenna 154 and a probe 156 is shown in FIG. 5A.

The antenna 154 may include a first planar substrate 170 and a second planar substrate 172 coupled to or adjacent each other. As shown, the first substrate 170 is coupled to the second substrate 172 using plastic rivets 174. Each substrate includes conductive portions 176 and nonconductive portions 178. The conductive portions 176 may be configured to receive (e.g., sample or measured) electromagnetic energy when being used as a collector antenna and to deliver electromagnetic energy of a particular polarity when being used as a transmitter antenna. The conductive portions 176 may include one or more conductive materials such as, e.g., copper, aluminum, silver, brass, gold, gold laminated copper, etc. In at least one embodiment, the conductive portions 176 include copper material. The nonconductive portions 178 may include one or more non-conductive materials such as, e.g., FR4, glass-reinforced epoxy, TEFLON® material, RT/DUROID® material, ARLON® material, ceramic material, etc. In at least one embodiment, the nonconductive portions 178 include ARLON DICLAD® 527 material.

The probe 156 may include conductive segments 159 and switchable segments 164. The conductive segments 159 may include one or more conductive materials such as, e.g., copper, aluminum, silver, gold, brass, etc. In at least one embodiment, the conductive segments 159 include copper. The probe 156 may be modulated (e.g., activated, inactivated, etc.) through the use of the switchable segments 164 (e.g., switches, embedded PIN diodes). More specifically, to increase the sensitivity of probe 156, five equally spaced switching PIN diodes may be used to implement the switchable segments 164 (e.g., the PIN diodes may be embedded on the probe 156 in series between the conductive segments 159). During modulation, or activation, of the probe, the diodes may be biased from reversed bias state, "off," to a forward bias state, "on." When the PIN diodes are in the reverse bias state, or "off," the probe 156 is invisible to electromagnetic fields (e.g., the scattered field). When the PIN diodes are in the forward bias state, or "on," the probe 156 is capable of interacting with electromagnetic fields parallel to its axis (or electromagnetic fields of the selected polarization).

The difference between two measured voltages by the antenna 154, one for each state of the probe 156, may be proportional to the field at the probe location. In other words, the difference between the measured voltage by the antenna 154 when the probe 156 is on, or active, and the measured voltage by the antenna 154 when the probe 156 is off, or inactive, may be proportional to the field at the probe location. If a modulated signal is employed to modulate the probes, the collected modulated signal may be proportional to the field at the probe location.

As mentioned, the antennas 156 may be connected to a RF multiplexer switch network, followed by a VNA, and a data acquisition program in the processing apparatus 112, which may control all the probes 156, antennas 154, etc. to acquire the scattered field data. As shown, the antenna assembly 152 may further include a connector block 158 operably coupled to the conductive portions 176 of the antenna 154, e.g., to connect the antenna to the RF multiplexer switch network.

In at least one embodiment, during a measurement, all probes 156 of antenna assemblies 152 that are not required for the measurement may be kept off, or inactive, making them invisible to the scattered field. The invisibility of these inactive probes 156 may circumvent any mutual coupling issues, and may further enable the use of many more probes 156 than the equivalent direct system having the same number of collector antennas 154.

Further, the use of one or more switchable segments 164 may make the probes 156 sufficiently invisible. The switchable segments 164 (e.g., PIN diodes) and their locations, however, may be calculated using an optimization algorithm that generates an accurate model for the given probe 156 (e.g., in at least one exemplary system, the optimal number of PIN diodes may be five). Moreover, biasing wires, which are connected to either ends of the probe 156, may be routed so as to incur a minimum amount of field interference as further described herein.

The biasing circuitry for each antenna (transmitter/collector) may be designed by numerical modeling of the antenna field distribution at various frequencies so as to determine the optimal routing of the biasing circuitry and wires. This modeling task may be performed for each type of antenna that is to be used in the exemplary systems described herein.

Figure 5B:
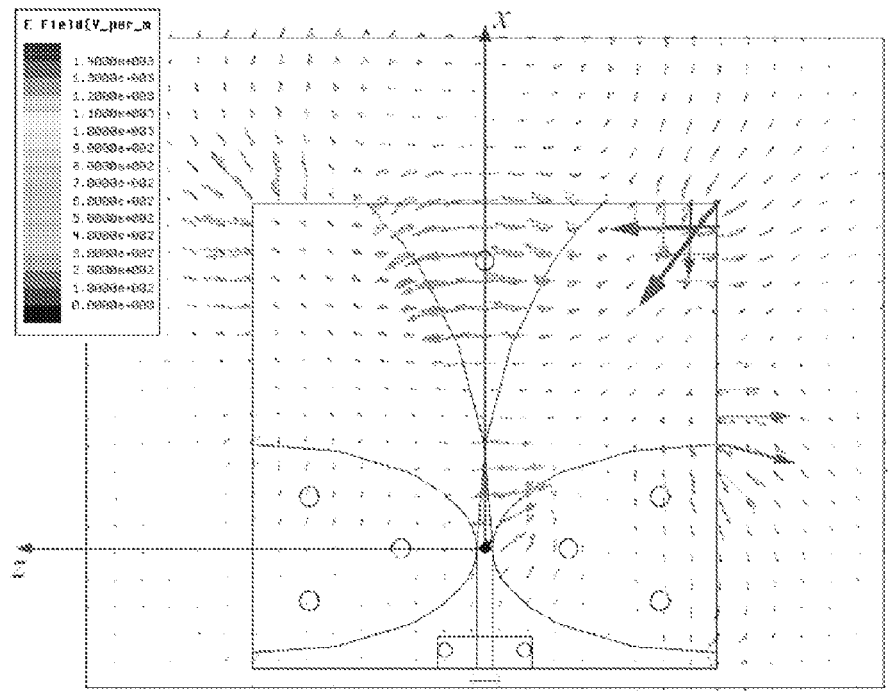
FIG. 5B is a depiction of an electromagnetic field distribution at 3.5 GHz within the antenna assembly of FIG. 5A.
Figure 5C:
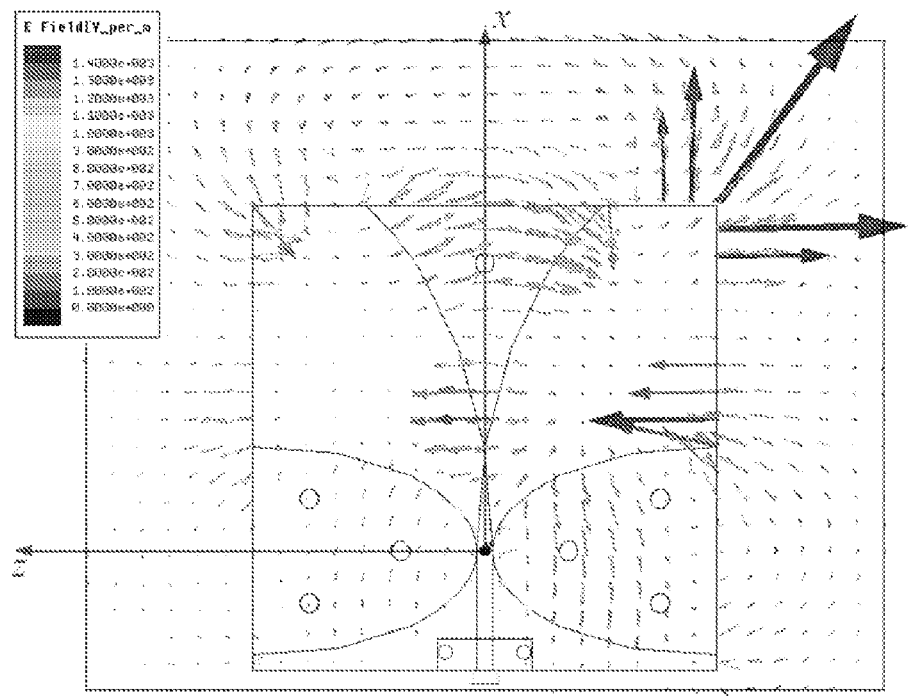
FIG. 5C is a depiction of an electromagnetic field distribution at 5.0 GHz within the antenna assembly of FIG. 5A.

For example, for the exemplary antenna 154 shown in FIG. 5A, the distribution of fields at 3.5 gigahertz (GHz) and 5.0 GHz are shown in FIG. 5B and FIG. 5C, respectively. As shown, the field intensity may be stronger at the corners of the antenna 154 and may be oriented in different directions. The central region of the antenna 154, however, may show a smaller variation of the field magnitude and the field vectors are, mostly, oriented along the z-axis. Based on these observations, and considering the probe length, biasing line paths 157 parallel to the x-axis between the nylon screws may be used to route biasing wires for the probe 156 as shown in FIG. 5A. In other words, the biasing wires may be routed based on the field distribution (e.g., along biasing line paths 157). Further, an adhesive may be used to secure the biasing wires to the antenna 156.

Figure 7:
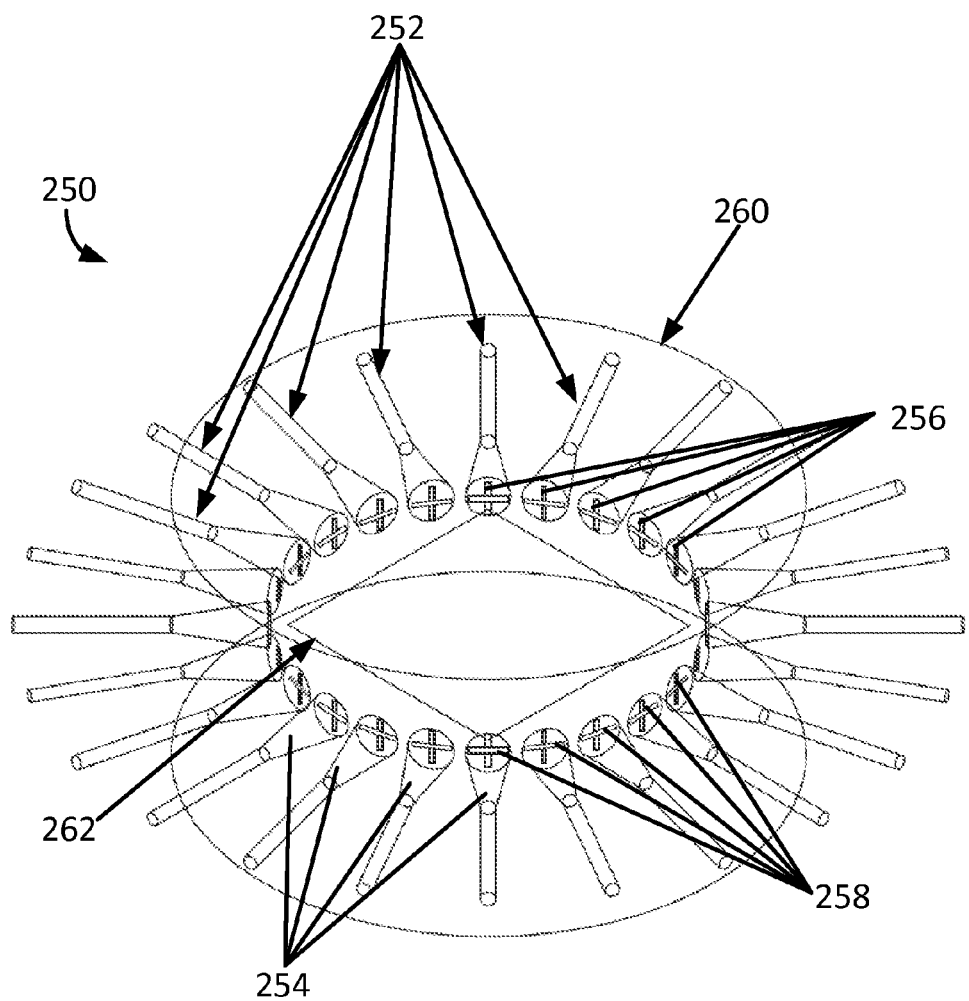
FIG. 7 is a perspective view of an exemplary dual-polarized imaging setup.

Similar analysis may be performed for exemplary horn-type antennas such as those described herein with reference to FIGS. 7-8. Moreover, two surface mounted "termination" resistors may be added to either side of the probe 156. These resistors may "terminate" the RF current at both ends of the probe 156. Using biasing line paths 157 shown in FIG. 5A, measurements showed that the changes of the reflection coefficient, due to the presence of the biasing wires may be less than 2 decibels (dB) within the frequency range of 1 GHz to 6 GHz. Additional routes, e.g., from the corners of the Vivaldi antenna, may yield interference with the Vivaldi antenna by more than 5 dB.

Figure 6A:
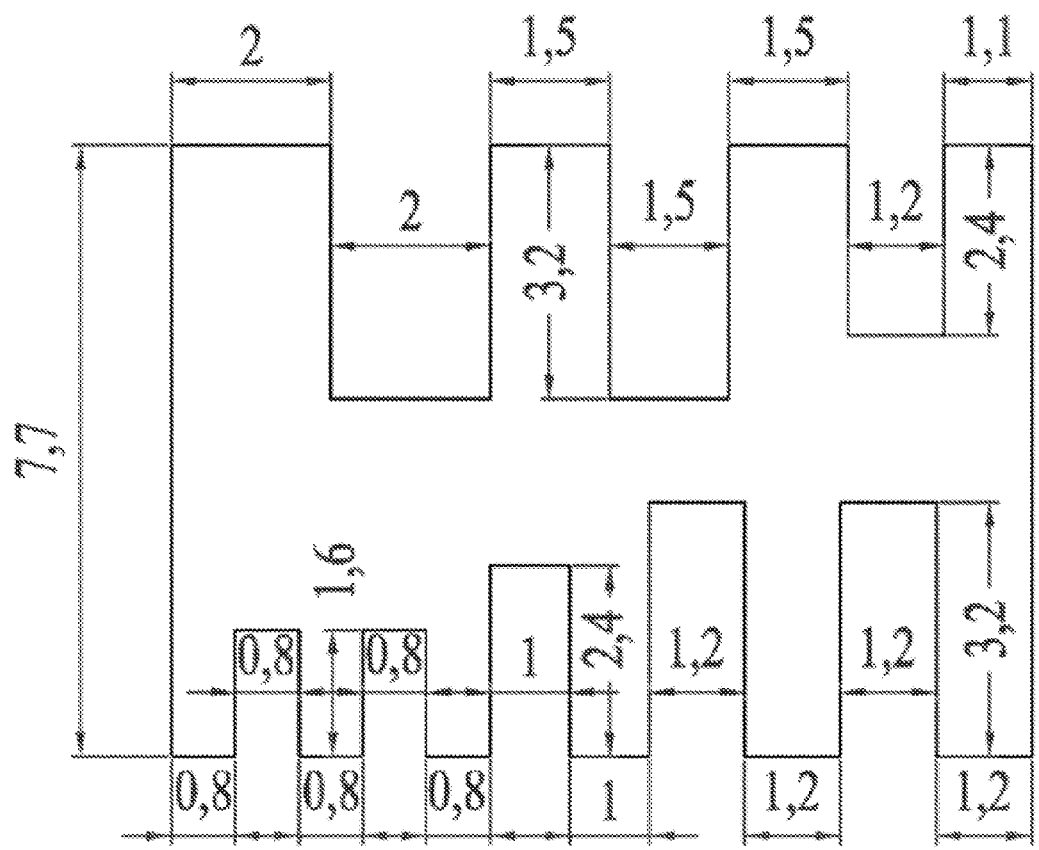
FIG. 6A is an exemplary object to be imaged, or object of interest.
Figure 6B:
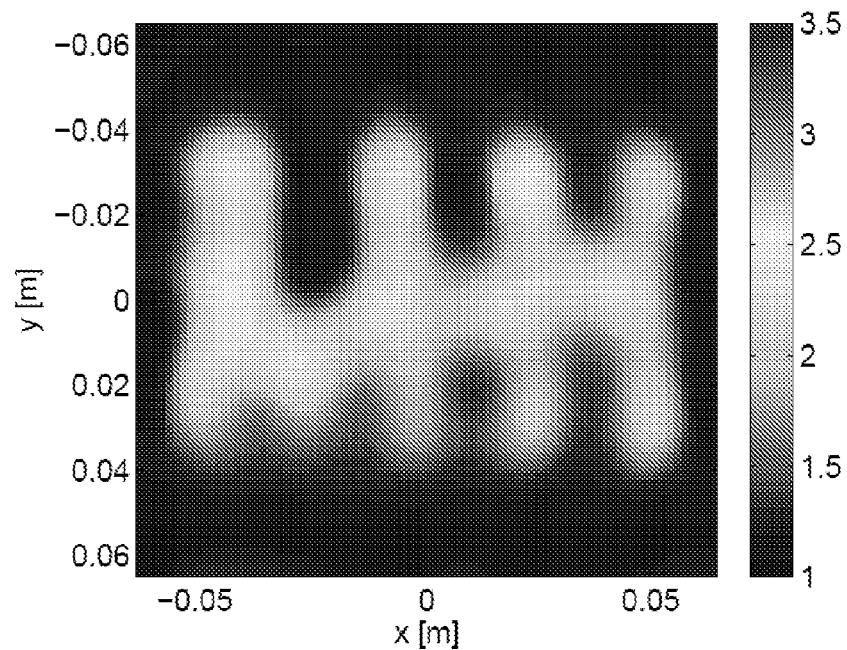
FIG. 6B is the real part of the dielectric permittivity of an exemplary reconstructed image of the object of FIG. 6A, e.g., using the single-polarized imaging setup of FIG. 4A.
Figure 6C:
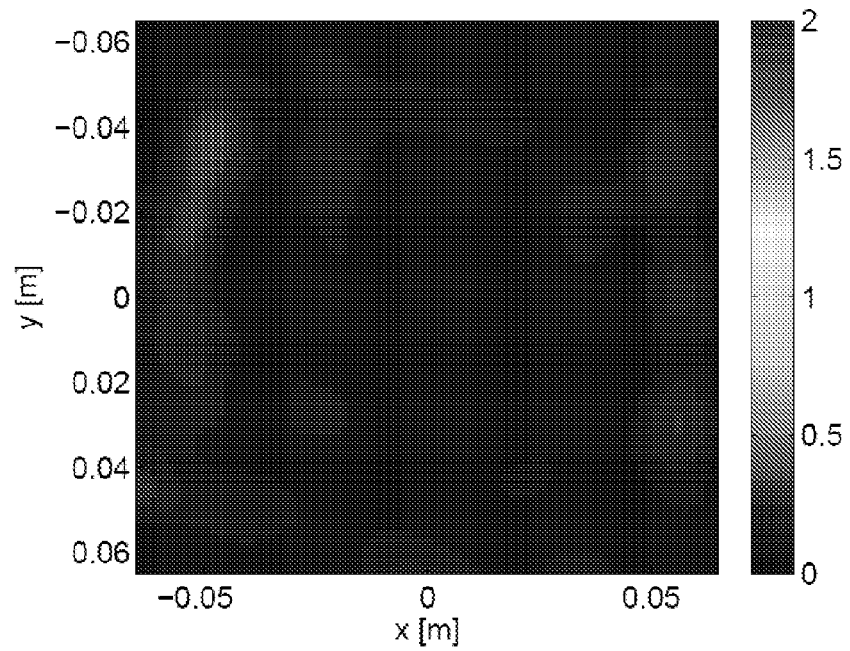
FIG. 6C is the imaginary part of the dielectric permittivity of an exemplary reconstructed image of the object of FIG. 6A, e.g., using the single-polarized imaging setup of FIG. 4A.

Using the exemplary methods and systems described herein, reconstructed images of the relative permittivity of OIs may be quantitatively reconstructed. Due to the wide frequency band of the antennas (e.g., DLVAs), multiple frequency inversion may also be achieved with this exemplary system. To test the exemplary system's imaging ability, a complicated object with relative complex permittivity of 2.3+j0 as depicted in FIG. 6A (dimensions are in centimeters) was imaged. The reconstructed quantitative image for the real part of the OI's permittivity is shown in FIG. 6B and the reconstructed quantitative image for the imaginary part of the OI's permittivity is shown in FIG. 6C.

In the exemplary system depicted in FIGS. 4A-4B, antennas 154 and the number of probes 156 are equal (e.g., each antenna assembly 152 includes one antenna 154 and one probe 156). Exemplary systems with unequal number of probes and antennas in the framework of a single-polarized imaging system may also be contemplated.

An exemplary dual-polarized imaging setup 250 including a plurality of antenna assemblies 252 utilizing horn antennas 254 is depicted in FIG. 7. The system may include a measurement chamber 260, which may be a metallic chamber and may be filled with high permittivity materials such as water for imaging of biological tissues. In at least one embodiment, the measurement chamber 260 may include nonconductive material such as, e.g., PLEXI-GLAS® material. In at least one embodiment, the measurement chambers for use in the exemplary imaging systems and methods described herein may be filled with materials having dielectric constants that are similar to the object being imaged (e.g., a matching fluid). For example, if the object to be imaged is an arm, the measurement chamber may be filled with a fluid having a dielectric constant similar to that of an arm.

The antenna assemblies 252 of the exemplary imaging setup 250 of FIG. 7 may further include vertical-polarized probes 256 (e.g., configured to interact with vertically polarized electromagnetic energy) and horizontal-polarized probes 258 (e.g., configured to interact with horizontally polarized electromagnetic energy) mounted in front of each horn antenna 254. Using the exemplary imaging setup 250 of FIG. 7, an image of an object of interest located in the imaging domain 262 may be reconstructed.

As shown, the exemplary imaging setup 250 includes twenty-four antenna assemblies 252, each including an antenna 254 (e.g., a transmitting and collecting antenna), a vertical probe 256, and a horizontal probe 258. When only considering linear polarizations, 24×23=552 data points may be collected for each polarization (e.g., when one antenna 254 is transmitting, the other antenna assembly 252, including each probe 256, 258 may gather data).

Further, in at least one embodiment, the probes may be located at different heights and locations, and therefore, may be used to create a three-dimensional imaging system. For example, the probes and/or antennas may be located at different heights vertically along the measurement chamber cylinder 260.

In the exemplary system depicted in FIG. 7, each antenna 254 may be slanted 45 degrees from the vertical direction (i.e., the vertical polarization) to generate, and to sample, a slant polarization. The use of slant polarity, or slant polarization, may enable one to illuminate the OI and to sample the scattered field in more than one selected polarity (e.g., a plurality of polarizations). For example, the use of slant polarity may enable the illumination and sample, of both the transverse-magnetic (TM) and transverse-electric (TE) polarizations. Further, each antenna 254 may further be configured to utilize general elliptic polarizations.

Figure 8A:
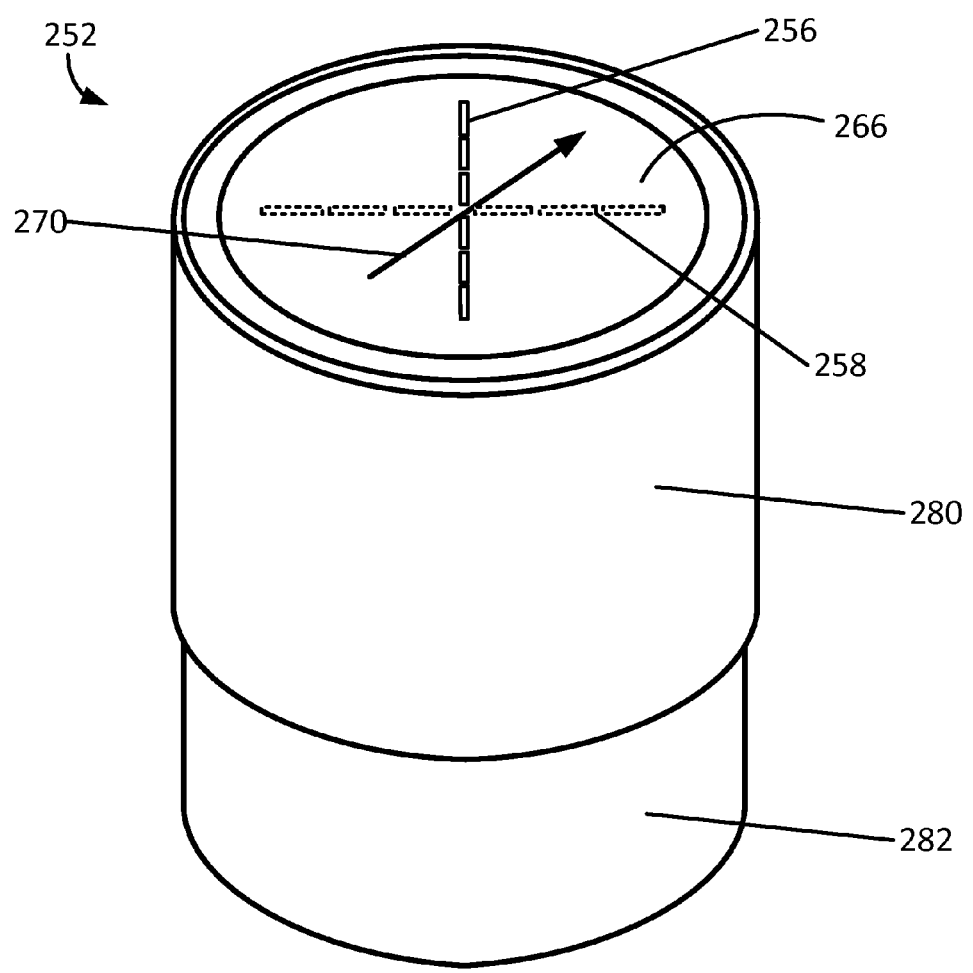
FIG. 8A is a perspective view of an exemplary dual-polarized antenna assembly, e.g., for use in the imaging setup of FIG. 7.
Figure 8B:
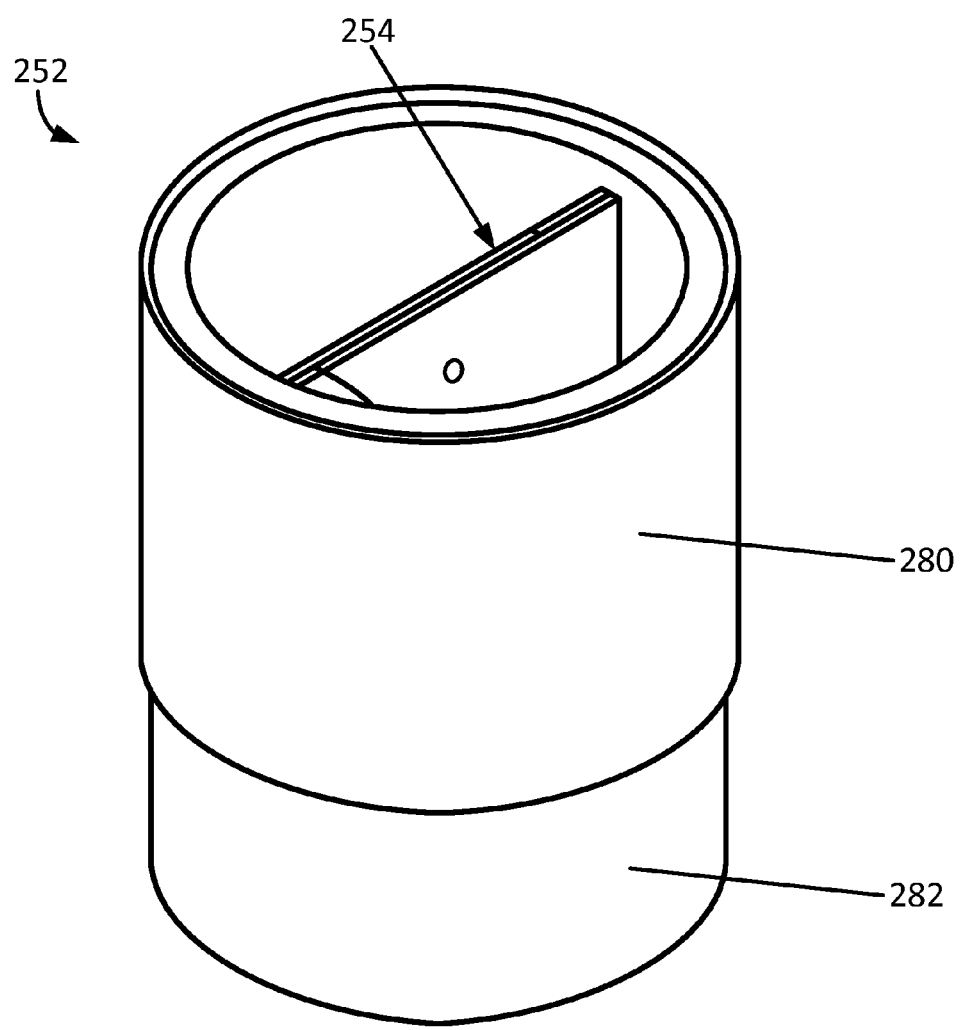
FIG. 8B is a perspective view of the dual-polarized antenna assembly of FIG. 8A without the probe portion.
Figure 8C:
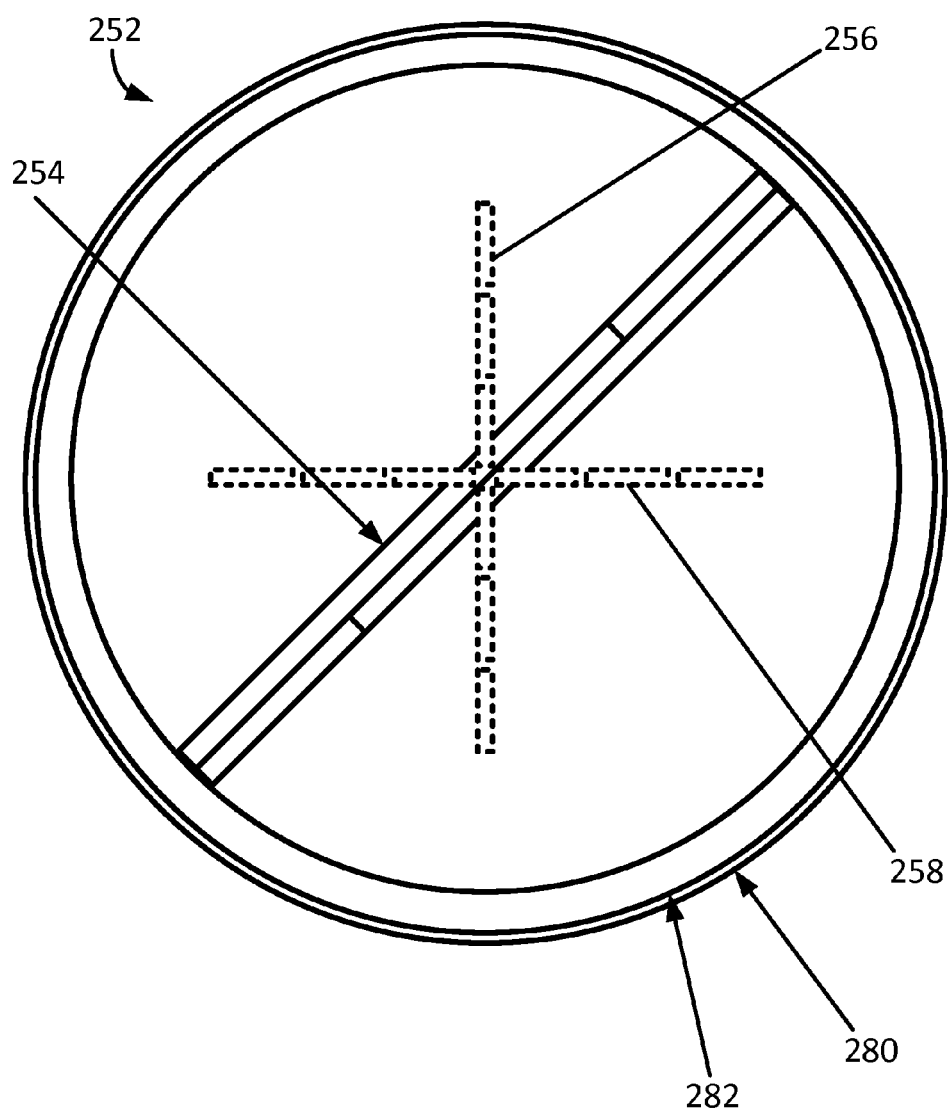
FIG. 8C is a top view of the dual-polarized antenna assembly of FIG. 8B with the location of the probes being represented by dotted lines.

As shown better in FIGS. 8A-8C, in order to capture each polarization, a vertical-polarized probe 256 may be etched on one side of a thin substrate 266 (parallel to the vertical polarization) and a horizontal-polarized probe 258 may be laminated on the other side of the substrate 266 (the horizontal-polarized probe 258 is shown in dotted lines since it is on the other side of the substrate 266). The substrate 266 may be located close to each antenna 254, e.g., such that the antenna 254 may measure the signal from the probes 256, 258. The substrate 266 and the probes 256, 258 located thereon are not depicted in FIGS. 8B-8C but the probes 256, 258 locations are depicted using dotted lines. As described herein, the probes 256, 258 closest to a particular antenna 254 may be referred to as being closely coupled to that antenna 254.

Similar to the exemplary single-polarized system of FIGS. 4A-4B, the antenna assemblies 252 may be configured to encircle the OI, and each antenna 254 of the antenna assemblies 252 may be used as a collector, or collecting antenna, when any of its corresponding scattering probes 256, 258 are active or inactive. In at least one embodiment, when an antenna assembly 252 is in a receiver mode, the vertical or horizontal polarized probes 256, 258 are sequentially activated to pick up the vertical or horizontal fields at their location, respectively.

As described herein, each probe 256, 258 may be biased by a pair of thin wires that extend perpendicular to the antenna polarization 270 shown in FIG. 8A. Being perpendicular to the antenna polarization 270, the biasing wires may not perturb the scattered field and the probes 256, 258.

In at least one embodiment, the biasing wires can be fiber optic, which do not interfere with the high frequency microwave signal, or they can be conductive wires, which, depending on their arrangement, may perturb the field. Further, interference may be minimized by either using absorber materials behind the probes (see, e.g., U.S. Pat. No. 5,430,369 to Bolomey et al.) or using a perfect electric conductor surface on top of the biasing circuitry (see, e.g., U.S. Pat. No. 7,746,266 to Zoughi et al.).

The antenna assembly 252 may further include a cylindrical housing 282 within which the antenna 254 is located. The cylindrical housing 282 may include one or more non-conductive materials such as, e.g., polymer, TEFLON® material, plastic, etc. In at least one embodiment, the cylindrical housing 282 may include Acrylonitrile Butadiene Styrene (ABS) plastic.

The cylindrical housing 282 may further be electromagnetically shielded using a conductive shielding 280. The conductive shielding 280 may include one or more conductive materials such as, e.g., copper, brass, aluminum, silver, etc. In at least one embodiment, the conductive shielding 280 may include copper. The conductive shielding 280 may reduce mutual coupling between adjacent antennas 254, and may reduce any perturbance of the probe biasing circuitry.

Exemplary imaging algorithms described herein may not model the antennas, the probes, or the entire 3D measurement system, which may result in modeling error. In most of MWT algorithms, the field excitation is implemented by a line-source (e.g., sometimes referred to as a point-source in 2D problems) placed at the transmitting antenna's location instead of an antenna in the presence of co-resident antenna, which may be another source of modeling error. Finally, in addition to modeling error, measurement errors may also be taken into account.

To reduce the effects of these errors, data collected by the horizontal probes or vertical probes should be calibrated. To calibrate the data, a Perfect Electric Conductor (PEC) cylinder may be used as a reference object (e.g., any well-defined object with known scattering behavior may be used). The scattered field produced by a PEC cylinder may be collected using the exemplary methods described herein. Afterwards, for any transmitter, an individual calibration factor may be defined for each probe for each frequency of operation. The calibration factor at each probing site may be the ratio of analytical scattered field by the reference object to the measured scattered field at that probe's location. The calibrated measured scattered field data, when imaging an arbitrary OI, may be obtained by multiplication of the measured data with the calibration coefficients. Then, the calibrated scattered field may be used by the exemplary inversion algorithm to reconstruct the relative complex permittivity of the OI and generate a quantitative image.

Single Polarization Example

An exemplary single polarized system is described herein with reference to FIGS. 9-14. The exemplary system may include four subsystems: a measurement chamber and a plurality of antennas; a RF multiplexer and VNA; a probe driver circuit; and controller computer.

The plurality of antennas may include 24 DLVAs mounted on a measurement chamber, which is a Plexiglas cylinder, 50.8 centimeters (cm) tall, with equal angular spacing of 15°. Each DLVA may be designed for an ultra-wideband frequency range of 3.1 to 10.6 GHz, and may include two layers held together by 7 Nylon screws. Compared to a single layer Vivaldi antenna, a double layer Vivaldi antenna may present at least a 10 dB improvement in cross polarization performance (see, e.g., M. Ostadrahimi, S. Noghanian, and L. Shafai, "A modified double layer tapered slot antenna with improved cross polarization," in Antenna Tech. and App. Electromagn. ANTEM/URSI. 13th Int. Symp. on IEEE, 2009, which is incorporated by reference herein in its entirety), which may be advantageous in the exemplary imaging algorithm (e.g., which assumes a two-dimensional (2D) transverse magnetic field distribution or simply assumes that only $E_z$ exists). The overall size of each DLVA may be 7 cm by 7 cm.

An exemplary direct experimental system using similar DLVAs may be described in C. Gilmore, P. Mojabi, A. Zakaria, M. Ostadrahimi, C. Kaye, S. Noghanian, L. Shafai, S. Pistorius, and J. LoVetri, "A wideband microwave tomography system with a novel frequency selection procedure," IEEE Trans. Biomed. Eng., vol. 57, no. 4, pp. 894-904, 2010, which is incorporated herein by reference in its entirety. The DLVAs in this exemplary system, however, are additionally equipped with a scattering probe located at a distance of 3 millimeters (mm) in front of the antenna. The imaging region is a square centered in the measuring chamber.

A 2 to 24 port RF electromechanical multiplexer (e.g., an Agilent 85070A) may be used to switch to a chosen active transmitting or receiving antenna. The isolation between ports may be 95 dB. The multiplexer may be connected to 2 ports of an Agilent 5071C VNA. The multiplexer and the VNA may be both controlled by the data acquisition program via the controller computer unit. Their connection may be established through a General Purpose Interface Bus (GPIB).

In order to switch the probes to closed/open (e.g., on/off, active/inactive, etc.), which correspond to forward/reverse biases of PIN diodes, respectively, a probe driver circuit including a 24 Darlington-pair transistor array may be used. The transistors may be connected to a 24-port USB I/O card, which may be controlled by the data acquisition program. Using high precision resistors, the forward bias current for all 24 probes may be adjusted with less than 1% tolerance.

A data acquisition program running on a controller computer may control all the instruments of the exemplary system. The controller computer may be directly connected to the probe driver circuit module via a USB connection. The multiplexer and the VNA may be connected through a GPIB-Ethernet hub. For collecting each dataset, a transmitting antenna may be chosen by switching it to one of the VNA ports. For each transmitting antenna, the other 23 receiving antennas may be switched sequentially to the second port of the VNA resulting in 24×23=552 measurements at each frequency. Each collector, or receiving antenna, may be configured to collect two measurements: one with the nearest probe (e.g., the closely coupled antenna) closed and another with the nearest probe (e.g., the closely coupled antenna) opened. More specifically, when the probe is closed (e.g., active and affecting the scattered electromagnetic field), the collector may measure the resultant scattered field that is affected by the probe, and when the probe is open (e.g., inactive and invisible to the scattered electromagnetic field), the collector may measure the resultant scattered field that is unaffected by the probe. By comparing these two measurements, the scattered field at the probe may be determined. Further, during these two measurements, the remaining probes are kept open (i.e., inactive or off), and thus, will have minimal effects on the measurements. The total data acquisition time for each frequency may be less than 4 minutes, which may be presently limited to the mechanical RF-switch settling time.

Each scattering probe may include a printed dipole on a small piece of substrate of the same type as is used for the DLVA (e.g., Arlon DiClad 527, thickness 62.5 mil having a relative permittivity of 2.5). The probe length and width may be 42.8 mm and 0.5 mm, respectively, which corresponds to a half-wavelength at 3.505 GHz.

To allow the opening and closing of each probe, 5 PIN diodes may be located in series at equally spaced positions on the probe. Further, each probe substrate may be attached to a DLVA using two small Nylon screws (2 mm). The distance between the probe and the DLVA may be 3 mm with the probe co-polarized with the DLVA.

Figure 9:
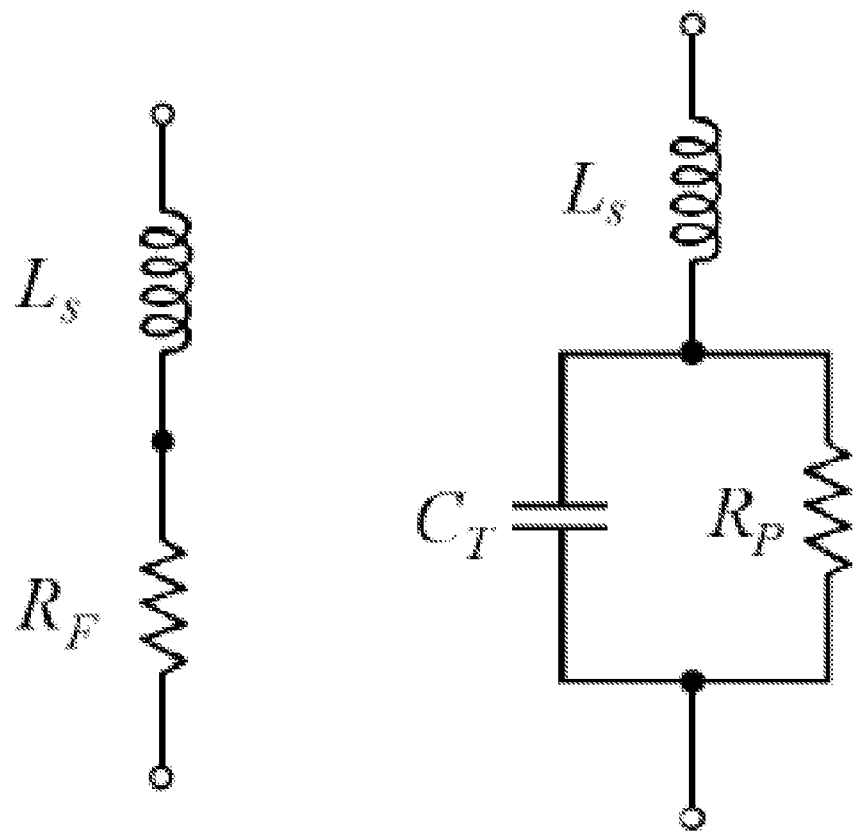
FIG. 9 is a PIN diode equivalent circuit model for the forward and reversed bias cases.

The PIN diode equivalent circuit model for the forward and reverse bias cases is shown in FIG. 9. The PIN diodes to be used in this exemplary system may be BAR64-02V PIN diodes from Infineon.

In order to model the presence of the PIN diodes, a simulation method that combines a full wave solver and a circuit simulator may be used. Developing such a combined simulation tool may further enable the calculation of the equivalent circuit of the PIN diode using an optimization method. The $S_{21}$ coefficient of the diode on a 50Ω transmission line is provided by the factory. The Ansoft Nexxim circuit solver may be used to simulate the circuit (as shown in FIG. 9) and the Ansoft HFSS Finite Element Method (FEM) solver may be used to simulate a 50Ω microstrip transmission line. Using the combined simulation, which may be referred to as the circuit-FEM solver and the quasi-Newton optimization technique, the equivalent circuit components may be calculated. The optimized values are listed in Table I.

TABLE I

DIODE CALCULATED EQUIVALENT CIRCUIT PARAMETERS.

| Symbol | Value |
|---|---|
| $R_F$ | 0.5 Ω |
| $L_s$ | 0.6 nH |
| $R_p$ | 4.0 KΩ |
| $C_T$ | 0.0718 pF |

Figure 10:
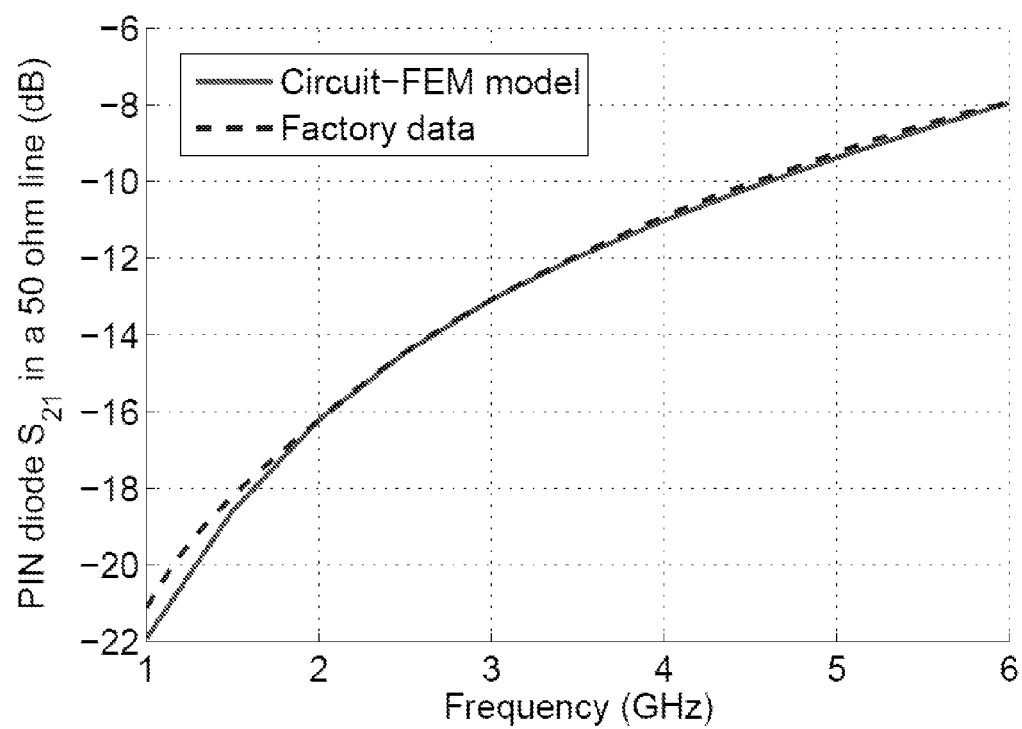
FIG. 10 is a graph of a PIN diode reverse bias insertion loss, comparing its factory measured data with the one obtained from an equivalent circuit model.
Figure 11:
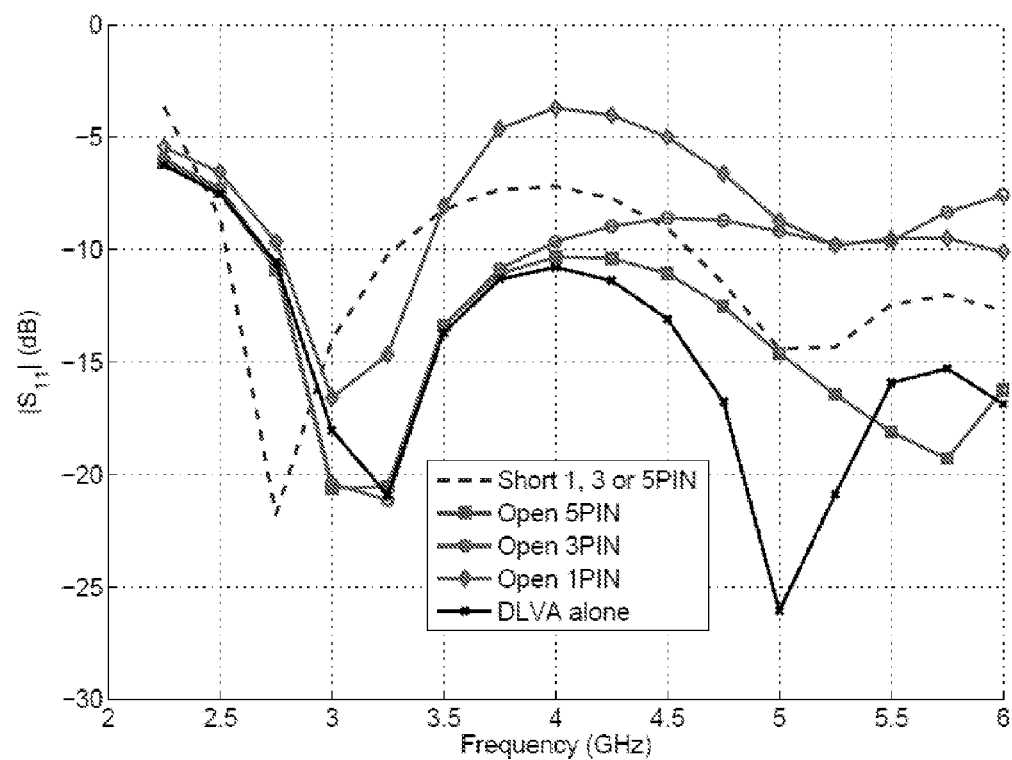
FIG. 11 is a graph of simulated reflection coefficients of a Double-Layered Vivaldi Antenna (DLVA) near a probe when changing the number of diodes on the probe.

A comparison of the calculated $S_{21}$ and the factory data are shown in FIG. 10, which illustrates agreement between the results.

Using the circuit-FEM solver, the reflection coefficient of the DLVA may be simulated in two cases: 1) when the probe is closed (i.e., forward biased diodes); and 2) when it is opened (i.e., reversed biased diodes).

The effect of using a different number of PIN diodes was simulated. For this study, 3 different simulations were performed: 1) a probe with single diode located at its center; 2) a probe with 3 diodes in series; and 3) a probe with 5 diodes in series, located equally spaced along the probe.

In the closed case, the changes of reflection coefficient for the 3 cases were negligible (less than 0.2 dB), which may be due to the small insertion loss of the PIN diodes.

In the open case, increasing the number of PIN diodes resulted in a performance more similar to the DLVA alone. These results are compared in FIG. 11. According to this comparison, it may be concluded that increasing the number of PIN diodes may decrease the interference of the generated fields of the DLVA in transmitting mode. Thus, a 5-PIN diode configuration was used in the exemplary system.

The bias current may be a DC current, which does not interfere with RF signals. The biasing circuitry and wires, however, may be designed to not significantly perturb the RF fields. In this example, the FEM method (Ansoft HFSS) was used to numerically model the field distribution in the vicinity of the DLVAs, at various frequencies, so as to determine the optimal routing of the fields at 3.5 GHz and 5.0 GHz. As shown in FIGS. 5B-5C, the field intensity may be stronger at the corners of the biasing circuitry and wires. However, a central region shows a smaller variation of fields, and the field vectors are, mostly, along the z-axis. Based on these observations, and considering the probe length, a bias line parallel to the x-axis, between the nylon screws, was used in the exemplary system.

Rosin may be used as the adhesive to secure the biasing wires to the DLVA. Further, two surface mounted "termination" resistors were added to the either side of the probe. These resistors "terminate" the RF current at both ends of the probe. Using this configuration, the measurements showed that the changes of the reflection coefficient, due to the presence of the biasing wires, may be less than 2 dB within the frequency range of 1 GHz to 6 GHz. Additional routes were also tried, e.g., from the corners of the DLVA; however, results showed that the biasing wires along these additional routes interfered with the DLVA by more than 5 dB.

For the imaging algorithm, the field scattered by the OI may be measured at each probe location. Each measurement at a probe's location may be performed by changing the impedance of the probe. The probe whose impedance was changed was referred to as the active probe. When a probe is active, the remaining probes are kept "open" so that they remain "invisible" to electromagnetic fields. The impedance change produces change in the measured voltage at the nearest collector (receiver DLVA), which may be proportional to the field at the active probe's location.

To measure the scattered field, the total field (i.e., with the OI present in the measurement chamber) and the incident field (i.e., with the OI absent in the measurement chamber) were collected. Thus, with one DLVA transmitting, the impedance of each active probe was changed by opening and closing its diodes, while keeping all of the remaining probes open. The transmitting DLVA may be connected to one port of the VNA while the nearest collector to the active probe (receiving DLVA) is connected to the second port of the VNA. The impedance change of the active probe in front of the collector generates a change in VNA transmission coefficient $S_{21}$ between the transmitting DLVA and the collector. Denoting the measured scattering parameters in the two cases of closing and opening the active probe as $S_{21}^{sc}$ and $S_{21}^{oc}$ respectively, the difference between these two measurements may be defined as $\delta S_{21} = S_{21}^{sc} - S_{21}^{oc}$.

Once the incident (no OI present) and total (OI present) fields were measured, the scattered field generated by the OI may be calculated by subtracting the total and incident fields: $E_z^{sct} = E_z^{tot} - E_z^{inc}$. The total and incident fields are thus proportional to $\delta S_{21}^{tot}$ and $\delta S_{21}^{inc}$, respectively, and thus the scattered field due to the object of interest satisfies:

$$E_z^{sct} \partial \delta S_{21}^{sct} \text{ where } \delta S_{21}^{sct} = \delta S_{21}^{tot} - \delta S_{21}^{inc}.$$

In the exemplary system, the probes are parallel to the z direction and interact mainly with $E_z$. A current may be generated on the probe that is proportional to the $E_z$ field component. The measurement procedure may be based on the assumption that the differential $\delta S_{21}$ is proportional to the field at the probe's location (for theoretical background, see, e.g., J. Bolomey and F. Gardiol, Engineering applications of the modulated scatterer technique. Artech House Publishers, 2001, which is incorporated by reference herein in its entirety).

One DLVA acting as both transmitting antenna and receiving antenna while a probe is located in front of it was further simulated. Using Ansoft HFSS, two simulations were performed: 1) computing the $E_z$ fields of a DLVA at different locations without the presence of any probe; and 2) computing the field with a probe parallel to the z-axis. In this simulation, the DLVA differential reflection coefficient $\delta S_{11}$ was computed for every location of the probe. The results of the two simulations agreed with each other.

Note that the measurement procedure may be effective in removing some sources of experimental error, e.g., errors due to cable movement, as well as the noise generated in the multiplexer unit and the network analyzer. The time interval between the two measurements may be very short, and it may be assumed that the cables remain stationary and unchanged during this interval.

The exemplary 2D imaging algorithm may not model the antennas or the entire 3D measurement system, which may result in modeling error. Moreover, the field excitation may be implemented by a line-source placed at the transmitting antenna's location, instead of a DLVA in the presence of co-resident DLVAs, which may further result in modeling error. Finally, in addition to modeling error, measurement errors may also occur. To reduce the effects of these errors, the data collected by the probes may be calibrated.

Figure 12:
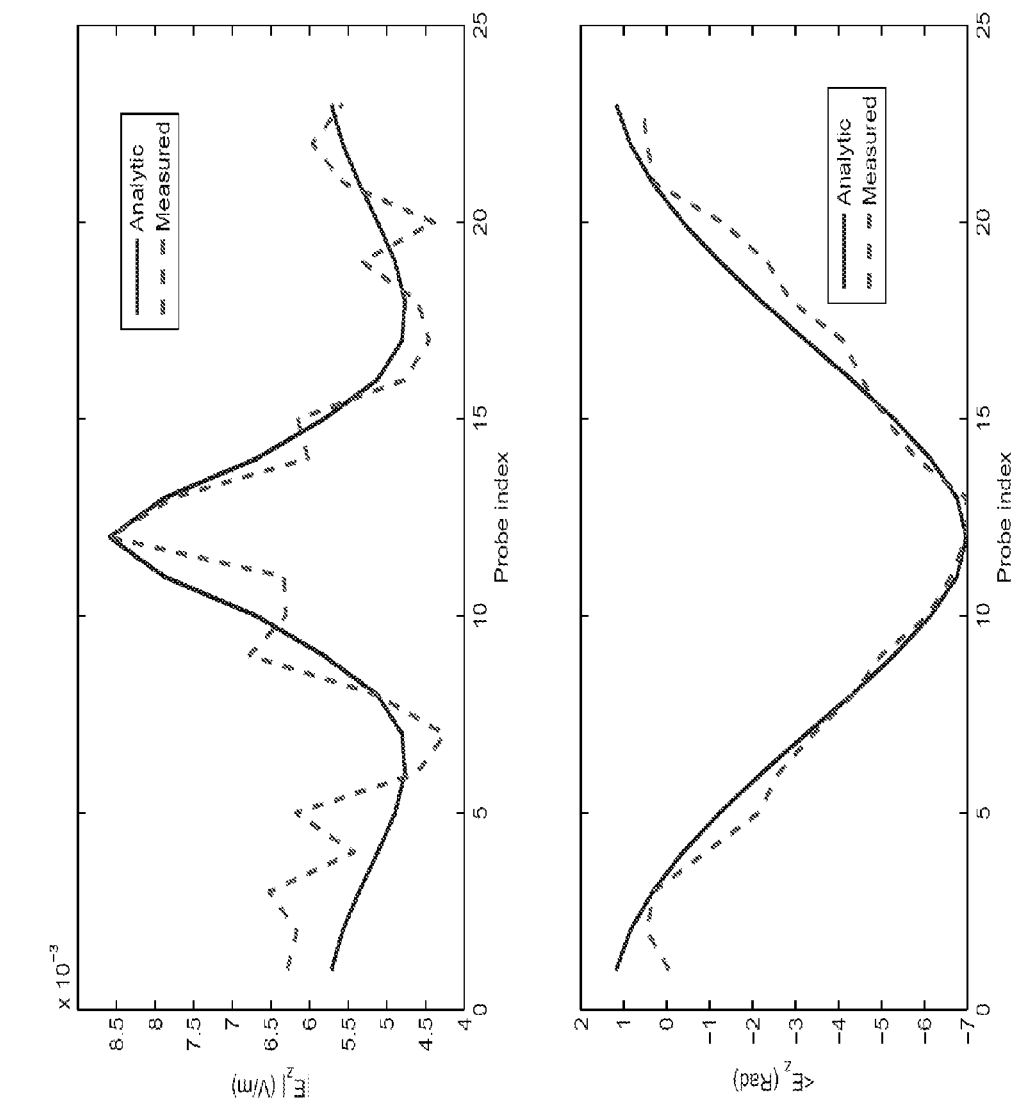
FIG. 12 includes graphs depicting comparisons of a scattered field by a reference perfect electric conductor (PEC) cylinder in an analytic solution and a scaled measurement at 4.5 GHz in the exemplary single-polarized imaging setup of FIG. 4A.

To calibrate the data, a Perfect Electric Conductor (PEC) cylinder may be utilized, 3.5 inches in diameter, as the reference object. The scattered field produced by this reference object may be collected using the measurement procedure as discussed herein. For any active transmitter antenna, an individual calibration factor may be defined for each probe. For example, 23×24=552 calibration factors may be defined for each frequency of operation in a 24 antenna, 24 probe system. For an active transmitter antenna, the calibration factor at each probing site, $C_F$, may be the ratio of analytical scattered field by the PEC cylinder to the measured scattered field at that probe's location:

$$C_F = E_z^{sct,analytic} / \delta S_{21}^{sct,PEC}$$

where $E_z^{sct,analytic}$ is the analytical solution of the scattered field by the PEC cylinder in the vicinity of a line source and $\delta S_{21}^{sct,PEC}$ is the measured data which is proportional to the actual scattered field in the presence of the PEC cylinder. A comparison of $E_z^{sct,analytic}$ and $\delta S_{21}^{sct,PEC}$ at 4.5 GHz is shown in FIG. 12.

552 calibration factors may be stored in the column vector $\underline{C_F} \in \mathbb{C}^{552}$. The set measured data $\delta S_{21}^{sct}$, which may represent the scattered field due to the OI at a given frequency, may also be stored in the column vector $\underline{\delta S_{21}^{sct}} \in \mathbb{C}^{552}$. The calibrated measured scattered field data, denoted by $\underline{E}^{meas}$, may then be obtained as $\underline{E}^{meas} = \underline{C_F} \odot \underline{\delta S_{21}^{sct}}$ where $\odot$ denoted the Hadamard product between two vectors of the same size. This calibrated measured scattered field may then be used by the inversion algorithm to reconstruct the relative complex permittivity of the OI.

Figure 13:
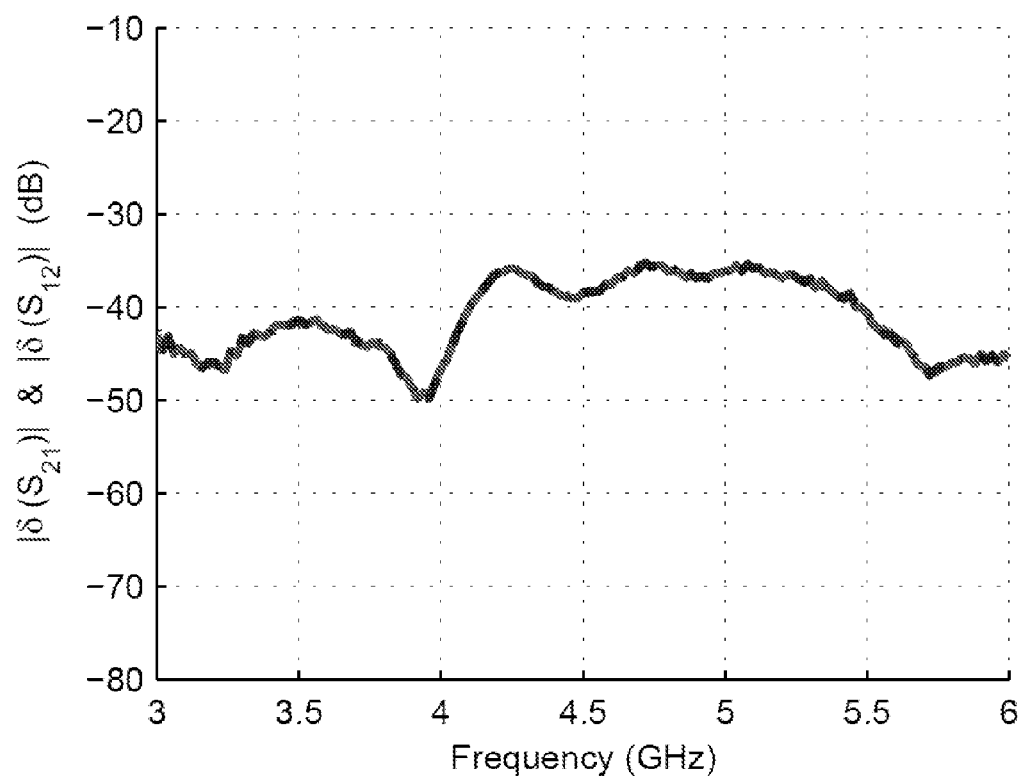
FIG. 13 is a graph of $\delta S_{21}$ for a transmitting antenna and receiving antenna(s) opposite the transmitting antenna with an incident power of −5 decibels per milliwatt (dBm) in the exemplary single-polarized imaging setup of FIG. 4A.

In order to measure the field at a probe location, the changes of the probe impedance may be detected by the VNA, which may be referred to as the sensitivity of the probe to the input power to the chamber. The incident field at each of the 24 DLVA locations may be measured while the VNA output power is set to −5 dBm. For each measurement, the impedance of the nearest probe to the receiver DLVA may be changed in order to record $\delta S_{21}$. Choosing the two antennas with greatest separation, that is, choosing antennas opposite from each other in the measurement chamber as the transmitter and the receiver, the lowest $\delta S_{21}$ was observed to be greater than −50 dB. This measurement is shown in FIG. 13 over the bandwidth of interest. For the same transmitting/receiving pair, which produced the lowest $\delta S_{21}$, the VNA output power was decreased from −5 dBm, in steps of 5 dB, down to the −35 dBm. At an output power level of −35 dBm, the measurements reached the noise floor, and thus, it was concluded that the probes are sensitive to an input power as low as −30 dBm. For this measurement, an averaging technique was not used to reduce the noise floor. In addition to $\delta S_{21}$ measurement, the change of reflection coefficient of the receiver antenna was measured, which is an indication of probe interaction with the receiver. The change of the reflection coefficient, $\delta S_{22}$, of one of the DLVAs in the measurement chamber when the nearest probe impedance was changed was further collected.

Figure 14:
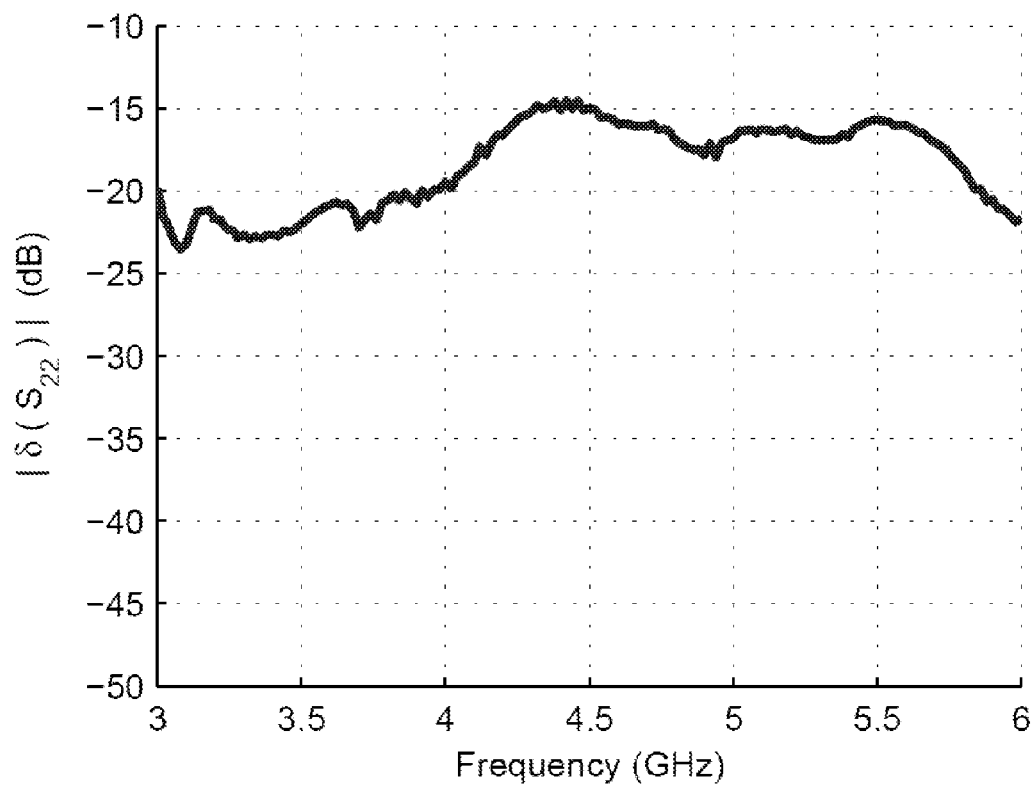
FIG. 14 is a graph of $\delta S_{22}$ measurement in a tomography system, as an indication of probe-DLVA interaction.
Figure 15:
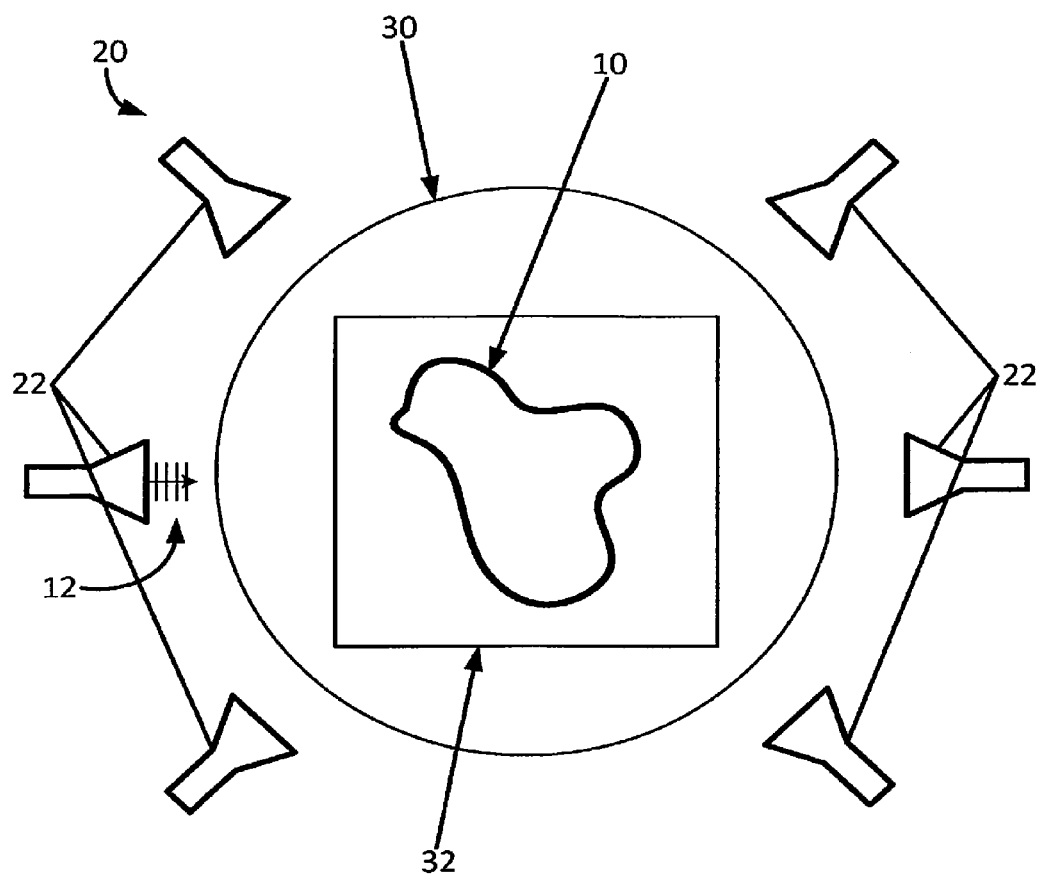
FIG. 15 is a prior-art imaging setup.

As shown in FIG. 14, the amplitude of the differential reflection coefficient may be in the range of −15 dB to −23 dB at the frequency range of 3 GHz to 6 GHz.

Averaging the measured data was also investigated to, e.g., improve the signal-to-noise ratio (SNR). For example, the signal may be averaged over a number of repeated measurements to obtain a higher SNR, such as, e.g., an averaged taken over 500 measurements may improve the SNR in the order of 25 dB in MWT systems (see, e.g., T. Henriksson, N. Joachimowicz, C. Conessa, and J. Bolomey, "Quantitative microwave imaging for breast cancer detection using a planar 2.45 GHz system," IEEE Trans. Instrum. Meas., vol. 59, no. 10, pp. 2691-2699, 2010, which is incorporated herein by reference in its entirety).

Several datasets using the proposed measurement system were collected. For each dataset, the fields were collected by applying the averaging of 1, 5, 10, 100, and 1000 times. The change of signal in all cases was less than 0.2 dB, while the VNA output power was set to −5 dBm. Negligible changes were observed in the datasets or in the images resulted from these datasets, and therefore, averaging may not be used, which may allow for faster one-shot data acquisition.

The imaging and measurement domains are denoted by D and S respectively, both of which are in $\mathbb{R}^2$. Also, r denotes the position vector in $\mathbb{R}^2$. The imaging domain may be immersed in a known background having relative complex permittivity of $\epsilon_b$, which contains a nonmagnetic OI with an unknown relative complex permittivity $\epsilon_r(r)$ (e.g., the background medium in this example is air). Assuming time dependency, the relative complex permittivity of the OI can be written as $\epsilon_r(r) = \epsilon'_r(r) - j\epsilon''(r)$. The contrast function, defined as $$\chi \triangleq \frac{\epsilon_r(r) - \epsilon_b}{\epsilon_b} \tag{2}$$

may be found using the measured scattered field on S. Once $\chi$ is found, the relative complex permittivity of the OI can be recovered. In the exemplary implementation, the contrast function may be discretized into N square pulses, and thus, the contrast function may be represented by the complex vector $\underline{\chi} \in \mathbb{C}^N$. Assuming the two-dimensional transverse magnetic illumination, the electric field can be represented by a single component perpendicular to the measurement and imaging domains. Denoting $\underline{E}^{meas}$ as the calibrated measured scattered field on S and $\underline{E}^{sct}(\underline{\chi})$ as the simulated scattered field on S due to the predicted contrast $\underline{\chi}$, the measurement problem may be formulated as the minimization over $\underline{\chi}$ of the following data misfit cost-functional:

$$F^{LS}(\underline{\chi}) = \frac{1}{\|\underline{E}^{meas}\|_S^2} \|\underline{E}^{sct}(\underline{\chi}) - \underline{E}^{meas}\|_S^2 \tag{3}$$

where $\|\cdot\|_S$ denotes the $L_2$-norm on S. The data misfit cost-functional, $F^{LS}(\underline{\chi})$, is nonlinear and ill-posed. Various methods, such as the modified gradient method (see, e.g., A. Abubakar, P. Van den Berg, and J. Mallorqui, "Imaging of biomedical data using a multiplicative regularized contrast source inversion method," IEEE Trans. Microw. Theory Tech., vol. 50, no. 7, pp. 1761-1771, 2002; R. Kleinman and P. Van Den Berg, "A modified gradient method for two-dimensional problems in tomography," Journal of Computational and Applied Mathematics, vol. 42, no. 1, pp. 17-35, 1992, each of which are incorporated by reference herein in their entireties) and the Gauss-Newton method (see, e.g., P. Mojabi and J. LoVetri, "Microwave biomedical imaging using the multiplicative regularized gauss-newton inversion," IEEE Antennas Wireless Propag. Lett, vol. 8, pp. 645-648, 2009; and W. Chew and Y. Wang, "Reconstruction of two-dimensional peimittivity distribution using the distorted born iterative method," Medical Imaging, IEEE Transactions on, vol. 9, no. 2, pp. 218-225, 1990, each of which are incorporated by reference herein in their entireties) may be used to treat the nonlinearity of this cost-functional. The ill-posedness of the problem may be further treated by employing an appropriate regularization technique (see, e.g., P. Mojabi and J. LoVetri, "Overview and classification of some regularization techniques for the gauss-newton inversion method applied to inverse scattering problems," IEEE Trans. Antennas Propag., vol. 57, no. 9, pp. 2658-2665, 2009, which is incorporated by reference herein in its entirety). For example, the weighted $L_2$-norm total variation multiplicative regularizer within the framework of the Gauss-Newton method may be utilized. The details of this method, which may be referred to as the Multiplicative Regularized Gauss-Newton Inversion (MR-GNI) method, may be found, e.g., in P. Mojabi and J. LoVetri, "Microwave biomedical imaging using the multiplicative regularized gauss-newton inversion," IEEE Antennas Wireless Propag. Left., vol. 8, pp. 645-648, 2009; and A. Abubakar, T. Habashy, V. Druskin, L. Knizhneman, and D. Alumbaugh, "2.5d forward and inverse modeling for interpreting low frequency electromagnetic measurements," Geophysics, vol. 73, 2008, each of which are incorporated by reference herein in their entireties.

Using the exemplary system and the exemplary MR-GNI algorithm, the relative complex permittivity of three different objects of interest (OIs) was imaged. These tests included the following tests: 1) a resolution test; 2) a combination test; and 3) a complexity test. The objects of interested were positioned at the center of the measurement chamber. The dataset was collected at the frequencies of 3 GHz to 5 GHz with a step of 0.5 GHz. For all cases, images of the OIs were successfully reconstructed. In addition to the single-frequency inversion, multiple-frequency inversion was also utilized to reconstruct the OIs. When using multiple-frequency inversion, the dielectric properties of the OIs were assumed to be invariant at all frequencies.

In the resolution test, two nylon rods whose separation is 4 mm were used as the OI. Each of the nylon rods had a diameter of 3.8 cm and were separated by 0.4 cm. The relative permittivity of nylon is 3.03-j0.03 ($\chi$=2.03 j0.03) (see, e.g., R. F. Harrington, Time-harmonic electromagnetic fields. New York: IEEE Press: Wiley-Interscience, 2001, which is incorporated by reference herein in its entirety). Further, for the resolution test, the imaging region is a 12 cm square and is discretized to 60×60 pixels. The real part of the nylons' reconstructed relative complex permittivity is close to its expected value (especially at 4.5 GHz). Further, the nylon rods are almost lossless, and thus, the inversion algorithm is not capable of reconstructing the imaginary part of the relative complex permittivity of the nylon rods due to limited signal-to-noise ratio and dynamic range of the system.

In the combination test, a combination of a PVC cylinder adjacent to a nylon rod was used as the OI. The PVC cylinder had an outside diameters of 13.0 cm and an inside diameter of 10.2 centimeters and the nylon rod had a diameter of 3.8 cm. The relative permittivity of PVC is $\in_r\approx$2.5-j0.01 at 4.5 GHz (see, e.g., C. Gilmore, P. Mojabi, A. Zakaria, S. Pistorius, and J. LoVetri, "On super-resolution with an experimental microwave tomography system," IEEE Antennas Wireless Propag. Left., vol. 9, pp. 393-396, 2010, which is incorporated herein by reference in its entirety). For the combination test, the imaging region was a 17 by 17 cm square and was discretized to 70×70 pixels. The multiple frequency reconstruction of this target was more accurate compared to its single-frequency reconstruction.

In the complexity test, a complex e-phantom object was used as shown in FIG. 6A. This object was first introduced in the following: S. Semenov, R. Svenson, A. Bulyshev, A. Souvorov, A. Nazarov, Y. Sizov, V. Posukh, A. Pavlovsky, P. Repin, and G. Tatsis, "Spatial resolution of microwave tomography for detection of myocardial ischemia and infarction-experimental study on two-dimensional models," IEEE Trans. Microw. Theory Tech., vol. 48, no. 4, pp. 538-544, 2000, which is incorporated herein by reference in its entirety. The e-phantom is made of UltraHigh Molecular Weight polyethylene (UHMW) with relative permittivity of $\in_r$=2.3. The loss of UHMW may be negligible (see, e.g., C. Gilmore, P. Mojabi, A. Zakaria, S. Pistorius, and J. LoVetri, "On super-resolution with an experimental microwave tomography system," IEEE Antennas Wireless Propag. Lett., vol. 9, pp. 393-396, 2010, which is incorporated herein by reference in its entirety).

For the complexity test, the imaging region was a 13 cm square and was discretized to 80 80 pixels. For multiple-frequency inversion, 3 GHz to 5 GHz with frequency step of 0.5 GHz is used. Similar to the results presented in C. Gilmore, P. Mojabi, A. Zakaria, S. Pistorius, and J. LoVetri, "On super-resolution with an experimental microwave tomography system," IEEE Antennas Wireless Propag. Lett., vol. 9, pp. 393-396, 2010 and S. Semenov, R. Svenson, A. Bulyshev, A. Souvorov, A. Nazarov, Y. Sizov, V. Posukh, A. Pavlovsky, P. Repin, and G. Tatsis, "Spatial resolution of microwave tomography for detection of myocardial ischemia and infarction-experimental study on two-dimensional models," IEEE Trans. Microw. Theory Tech., vol. 48, no. 4, pp. 538-544, 2000, each of which is incorporated herein by reference in its entirety, features with a minimum size of 1 cm and above may be resolved while the two concave features of 0.8 cm are not resolved.

A synthetic dataset with 3% additive white noise (according to the formula given in A. Abubakar, P. Van Den Berg, and S. Semenov, "A robust iterative method for born inversion," Geoscience and Remote Sensing, IEEE Transactions on, vol. 42, no. 2, pp. 342-354, 2004, which is incorporated herein by reference in its entirety) of the e-phantom (complexity test) was created. This synthetic data set may be created with the Method of Moments, using 24 line sources, positioned at the same location as the probes in the measurement system. The results of synthetic data inversion were compared with those of the measured data. Overall, the reconstruction results were similar; however, the quantitative accuracy of the reconstructed image from the synthetic data may be slightly higher than that from the measured data.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A method of imaging an object using microwave tomography, wherein the method comprises:
providing a plurality of antenna assemblies positioned about an object, wherein each antenna assembly of the plurality of antenna assemblies comprises:
an antenna, and
one or more probes spatially distributed relative to the antenna, wherein each probe of the one or more probes is configurable in an active state and an inactive state, wherein each probe interacts with electromagnetic energy when in the active state, wherein each probe is nonresponsive to electromagnetic energy when in the inactive state,
individually configuring each probe of the one or more probes of the plurality of antenna assemblies in the active state while configuring the remaining probes of the one or more probes of the plurality of antenna assemblies in the inactive state until each probe of the one or more probes of the plurality of antenna assemblies has been individually configured in the active state;
delivering electromagnetic energy using the antenna of at least one antenna assembly of the plurality of antenna assemblies to irradiate the object resulting in scattered electromagnetic energy for each probe being configured in the active state;
sampling the scattered electromagnetic energy using the antenna of at least one antenna assembly of the plurality of antenna assemblies for each probe being configured in the active state; and
reconstructing an image of the object based on the sampled scattered electromagnetic energy.

2. The method of claim 1, wherein the one or more probes of the plurality of antenna assemblies comprise two or more probes.

3. The method of claim 1, wherein the one or more probes comprise:
a first probe configured to interact with electromagnetic energy of a first selected polarity when in the active state; and
a second probe configured to interact with electromagnetic energy of a second selected polarity when in the active state, wherein the first selected polarity is different than the second selected polarity.

4. The method of claim 3, wherein the first selected polarity is perpendicular to the second selected polarity.

5. The method of claim 3, wherein delivering electromagnetic energy using the antenna of the at least one antenna assembly of the plurality of antenna assemblies to irradiate the object comprises delivering electromagnetic energy at a slant polarity, wherein the slant polarity comprises components of the first selected polarity and the second selected polarity.

6. The method of claim 1, wherein the plurality of antenna assemblies comprises three or more antenna assemblies.

7. The method of claim 1, wherein each antenna assembly of the plurality of antenna assemblies is in a fixed position relative to the object.

8. The method of claim 1, wherein one or more of the plurality of antenna assemblies are configured to be attached to the object.

9. The method of claim 1, wherein the antenna and the one or more probes of each antenna assembly of the plurality of antenna assemblies are stationary with respect to each other.

10. The method of claim 1, wherein the plurality of antenna assemblies is positioned around a perimeter of the object and lie in a plane.

11. The method of claim 1, wherein delivering electromagnetic energy using the antenna of at least one antenna assembly of the plurality of antenna assemblies to irradiate the object resulting in scattered electromagnetic energy comprises individually delivering electromagnetic energy with the antenna of each antenna assembly of the plurality of antenna assemblies until the antenna of each antenna assembly has individually delivered electromagnetic energy.

12. The method of claim 1, wherein sampling the scattered electromagnetic energy using the antenna of at least one antenna assembly of the plurality of antenna assemblies further comprises sampling the scattered electromagnetic energy using the antenna of the antenna assembly of the plurality of antenna assemblies that comprises the probe configured in the active state.

13. The method of claim 1, wherein sampling the scattered electromagnetic energy using the antenna of at least one antenna assembly of the plurality of antenna assemblies further comprises sampling the scattered electromagnetic energy using the antennas of two or more antenna assemblies of the plurality of antenna assemblies.

14. The method of claim 13, wherein the sampled scattered electromagnetic energy using the antennas of two or more antenna assemblies of the plurality of antenna assemblies is combined in analog.

15. The method of claim 1, wherein each probe of the one or more probes of the plurality of antenna assemblies conductive segments comprises:
a plurality of conductive segments, and
a plurality of switchable segments coupling the conductive segments, wherein the switchable segments are configurable between a conducting configuration and a non-conducting configuration, wherein the plurality of conductive segments are electrically coupled via the switchable segments when the switchable segments are configured in the conducting configuration, wherein the plurality of conductive segments are electrically isolated from one another when the switchable segments are configured in the non-conducting configuration,
wherein the switchable segments are configured in the conducting configuration when the probe is in the active configuration, wherein the switchable segments are configured in the non-conducting configuration when the probe is in the inactive configuration.

16. The method of claim 1, wherein the reconstructed image is a quantitative image.

17. The method of claim 1, wherein the sampling is also performed by the antenna of each antenna assembly of the plurality of antenna assemblies when all the probes of the plurality of probes are configured in the inactive state to establish a baseline measurement for the antenna of each antenna assembly.

18. A system for use in imaging an object using microwave tomography, wherein the system comprises:
a plurality of antenna assemblies positionable about an object, wherein each antenna assembly of the plurality of antenna assemblies comprises:
an antenna configured to deliver electromagnetic energy to irradiate the object resulting in scattered electromagnetic energy and to sample scattered electromagnetic energy, and one or more probes spatially distributed relative to the antenna, wherein each probe of the one or more probes is configurable in an active state and an inactive state, wherein each probe interacts with electromagnetic energy when in the active state, wherein each probe is nonresponsive to electromagnetic energy when in the inactive state; and processing apparatus coupled to the plurality of antenna assemblies, wherein the processing apparatus is configured to:

individually configure each probe of the one or more probes of the plurality of antenna assemblies in the active state while configuring the remaining probes of the one or more probes of the plurality of antenna assemblies in the inactive state until each probe of the one or more probes of the plurality of antenna assemblies has been individually configured in the active state, initiate the delivery of electromagnetic energy using the antenna of at least one antenna assembly of the plurality of antenna assemblies to irradiate the object resulting in scattered electromagnetic energy for each probe being configured in the active state;

initiate the sampling of the scattered electromagnetic energy using the antenna of at least one antenna assembly of the plurality of antenna assemblies for each probe being configured in the active state; and reconstruct an image of the object based on the sampled scattered electromagnetic energy.

19. The system of claim 18, wherein the one or more probes of the plurality of antenna assemblies comprise two or more probes.

20. The system of claim 18, wherein the one or more probes comprise:
   a first probe configured to interact with electromagnetic energy of a first selected polarity when in the active state; and
   a second probe configured to interact with electromagnetic energy of a second selected polarity when in the active state, wherein the first selected polarity is different than the second selected polarity.

21. The system of claim 20, wherein the first selected polarity is perpendicular to the second selected polarity.

22. The system of claim 20, wherein delivering electromagnetic energy using the antenna of the at least one antenna assembly of the plurality of antenna assemblies to irradiate the object comprises delivering electromagnetic energy at a slant polarity, wherein the slant polarity comprises components of the first selected polarity and the second selected polarity.

23. The system of claim 18, wherein the plurality of antenna assemblies comprises three or more antenna assemblies.

24. The system of claim 18, wherein each antenna assembly of the plurality of antenna assemblies is in a fixed position relative to the object.

25. The system of claim 18, wherein one or more of the plurality of antenna assemblies are configured to be attached to the object.

26. The system of claim 18, wherein the antenna and the one or more probes of each antenna assembly of the plurality of antenna assemblies are stationary with respect to each other.

27. The system of claim 18, wherein the plurality of antenna assemblies is positioned around a perimeter of the object and lie in a plane.

28. The system of claim 18, wherein delivering electromagnetic energy using the antenna of at least one antenna assembly of the plurality of antenna assemblies to irradiate the object resulting in scattered electromagnetic energy comprises individually delivering electromagnetic energy with the antenna of each antenna assembly of the plurality of antenna assemblies until the antenna of each antenna assembly has individually delivered electromagnetic energy.

29. The system of claim 18, wherein sampling the scattered electromagnetic energy using the antenna of at least one antenna assembly of the plurality of antenna assemblies further comprises sampling the scattered electromagnetic energy using the antenna of the antenna assembly of the plurality of antenna assemblies that comprises the probe configured in the active state.

30. The system of claim 18, wherein sampling the scattered electromagnetic energy using the antenna of at least one antenna assembly of the plurality of antenna assemblies further comprises sampling the scattered electromagnetic energy using the antennas of two or more antenna assemblies of the plurality of antenna assemblies.

31. The system of claim 30, wherein the sampled scattered electromagnetic energy using the antennas of two or more antenna assemblies of the plurality of antenna assemblies is combined in analog.

32. The system of claim 18, wherein each probe of the one or more probes of the plurality of antenna assemblies conductive segments comprises:
   a plurality of conductive segments, and
   a plurality of switchable segments coupling the conductive segments, wherein the switchable segments are configurable between a conducting configuration and a non-conducting configuration, wherein the plurality of conductive segments are electrically coupled via the switchable segments when the switchable segments are configured in the conducting configuration, wherein the plurality of conductive segments are electrically isolated from one another when the switchable segments are configured in the non-conducting configuration,
   wherein the switchable segments are configured in the conducting configuration when the probe is in the active configuration, wherein the switchable segments are configured in the non-conducting configuration when the probe is in the inactive configuration.

33. The system of claim 18, wherein the reconstructed image is a quantitative image.

34. The system of claim 18, wherein the sampling is also performed by the antenna of each antenna assembly of the plurality of antenna assemblies when all the probes of the plurality of probes are configured in the inactive state to establish a baseline measurement for the antenna of each antenna assembly.

* * * * *